US011971465B2

(12) United States Patent
Hugon et al.

(10) Patent No.: US 11,971,465 B2
(45) Date of Patent: *Apr. 30, 2024

(54) FERROMAGNETIC FRAME FOR MAGNETIC RESONANCE IMAGING

(71) Applicant: Hyperfine Operations, Inc., Guilford, CT (US)

(72) Inventors: Cedric Hugon, Guilford, CT (US); Hadrien A. Dyvorne, New York, NY (US); Michael Stephen Poole, Guilford, CT (US)

(73) Assignee: Hyperfine Operations, Inc., Guilford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/884,078

(22) Filed: Aug. 9, 2022

(65) Prior Publication Data

US 2023/0095957 A1 Mar. 30, 2023

Related U.S. Application Data

(63) Continuation of application No. 17/116,173, filed on Dec. 9, 2020, now Pat. No. 11,422,213.
(Continued)

(51) Int. Cl.
*G01R 33/38* (2006.01)
*A61B 5/055* (2006.01)
(Continued)

(52) U.S. Cl.
CPC ............ *G01R 33/383* (2013.01); *A61B 5/055* (2013.01); *G01R 33/34092* (2013.01);
(Continued)

(58) Field of Classification Search
CPC ............ G01R 33/383; G01R 33/34092; G01R 33/385; G01R 33/3873; G01R 33/445; G01R 33/56518; A61B 5/055
See application file for complete search history.

(56) References Cited

U.S. PATENT DOCUMENTS

| | | |
|---|---|---|
| 4,498,048 A | 2/1985 | Lee et al. |
| 5,194,810 A | 3/1993 | Breneman et al. |
| | (Continued) | |

FOREIGN PATENT DOCUMENTS

| | | |
|---|---|---|
| EP | 0 479 278 A1 | 4/1992 |
| EP | 0 801 314 A1 | 10/1997 |
| | (Continued) | |

OTHER PUBLICATIONS

U.S. Appl. No. 17/116,173, filed Dec. 9, 2020, Hugon et al.
(Continued)

*Primary Examiner* — G. M. A Hyder
(74) *Attorney, Agent, or Firm* — Foley & Lardner LLP

(57) ABSTRACT

An apparatus for providing a $B_0$ magnetic field for a magnetic resonance imaging system. The apparatus includes at least one permanent $B_0$ magnet to contribute a magnetic field to the Bo magnetic field for the MRI system and a ferromagnetic frame configured to capture and direct at least some of the magnetic field generated by the $B_0$ magnet. The ferromagnetic frame includes a first post having a first end and a second end, a first multi-pronged member coupled to the first end, and a second multi-pronged member coupled to the second end, wherein the first and second multi-pronged members support the at least one permanent $B_0$ magnet.

20 Claims, 16 Drawing Sheets

Related U.S. Application Data

(60) Provisional application No. 62/946,000, filed on Dec. 10, 2019.

(51) Int. Cl.

| | | |
|---|---|---|
| *G01R 33/34* | (2006.01) | |
| *G01R 33/383* | (2006.01) | |
| *G01R 33/385* | (2006.01) | |
| *G01R 33/3873* | (2006.01) | |
| *G01R 33/44* | (2006.01) | |

(52) U.S. Cl.
CPC ....... *G01R 33/385* (2013.01); *G01R 33/3873* (2013.01); *G01R 33/445* (2013.01)

(56) References Cited

U.S. PATENT DOCUMENTS

| | | |
|---|---|---|
| 5,319,339 A | 6/1994 | Leupold |
| 5,659,250 A | 8/1997 | Domigan et al. |
| 5,886,070 A | 3/1999 | Honkura et al. |
| 6,340,888 B1 * | 1/2002 | Aoki .............. G01R 33/383 324/319 |
| 6,621,267 B1 * | 9/2003 | Damadian .............. A61B 5/055 324/319 |
| 6,970,061 B1 | 11/2005 | Danby et al. |
| 7,631,411 B2 | 12/2009 | Mao et al. |
| D703,322 S | 4/2014 | Hayman et al. |
| D742,519 S | 11/2015 | Sul |
| 9,224,526 B1 | 12/2015 | Nagarathnam et al. |
| 9,541,616 B2 | 1/2017 | Rothberg et al. |
| 9,547,057 B2 | 1/2017 | Rearick et al. |
| 9,625,543 B2 | 4/2017 | Rearick et al. |
| 9,625,544 B2 | 4/2017 | Poole et al. |
| 9,638,773 B2 | 5/2017 | Poole et al. |
| 9,645,210 B2 | 5/2017 | McNulty et al. |
| D790,709 S | 6/2017 | Gmeiner et al. |
| 9,797,971 B2 | 10/2017 | Rearick et al. |
| 9,817,093 B2 | 11/2017 | Rothberg et al. |
| D806,660 S | 1/2018 | Braswell, Jr. et al. |
| 10,139,464 B2 | 11/2018 | Rearick et al. |
| 10,145,913 B2 | 12/2018 | Hugon et al. |
| 10,145,922 B2 | 12/2018 | Rothberg et al. |
| 10,222,434 B2 | 3/2019 | Poole et al. |
| 10,222,435 B2 | 3/2019 | Mileski et al. |
| 10,241,177 B2 | 3/2019 | Poole et al. |
| 10,274,561 B2 | 4/2019 | Poole et al. |
| 10,281,540 B2 | 5/2019 | Mileski et al. |
| 10,281,541 B2 | 5/2019 | Poole et al. |
| 10,295,628 B2 | 5/2019 | Mileski et al. |
| 10,310,037 B2 | 6/2019 | McNulty et al. |
| 10,324,147 B2 | 6/2019 | McNulty et al. |
| 10,330,755 B2 | 6/2019 | Poole et al. |
| 10,353,030 B2 | 7/2019 | Poole et al. |
| 10,371,773 B2 | 8/2019 | Poole et al. |
| 10,379,186 B2 | 8/2019 | Rothberg et al. |
| 10,416,264 B2 | 9/2019 | Sofka et al. |
| 10,444,310 B2 | 10/2019 | Poole et al. |
| 10,466,327 B2 | 11/2019 | Rothberg et al. |
| 10,488,482 B2 | 11/2019 | Rearick et al. |
| 10,495,712 B2 | 12/2019 | Rothberg et al. |
| 10,520,566 B2 | 12/2019 | Poole et al. |
| 10,527,692 B2 | 1/2020 | McNulty et al. |
| 10,534,058 B2 | 1/2020 | Sofka et al. |
| 10,539,637 B2 | 1/2020 | Poole et al. |
| 10,545,207 B2 | 1/2020 | Poole et al. |
| D874,653 S | 2/2020 | Liu et al. |
| 10,551,452 B2 | 2/2020 | Rearick et al. |
| 10,564,239 B2 | 2/2020 | Poole et al. |
| 10,591,561 B2 | 3/2020 | Sacolick et al. |
| D889,467 S | 7/2020 | Fook |
| D890,927 S | 7/2020 | Chong |
| 10,709,387 B2 | 7/2020 | Poole et al. |
| 10,867,733 B2 | 12/2020 | Haham Hay |
| D912,822 S | 3/2021 | Hugon et al. |
| D932,014 S | 9/2021 | Hugon |
| 11,275,137 B2 | 3/2022 | Hugon et al. |
| 11,333,727 B2 | 5/2022 | Hugon et al. |
| 11,422,213 B2 | 8/2022 | Hugon et al. |
| 2006/0232369 A1 | 10/2006 | Gorshkov |
| 2007/0146107 A1 | 6/2007 | Lvovsky et al. |
| 2009/0128272 A1 | 5/2009 | Hills |
| 2012/0013338 A1 | 1/2012 | Sakellariou et al. |
| 2014/0111202 A1 | 4/2014 | Wald et al. |
| 2014/0111205 A1 | 4/2014 | Cazaux et al. |
| 2015/0260809 A1 | 9/2015 | Vidarsson |
| 2016/0069968 A1 | 3/2016 | Rothberg et al. |
| 2016/0069970 A1 | 3/2016 | Rearick et al. |
| 2016/0069971 A1 | 3/2016 | McNulty et al. |
| 2016/0069972 A1 | 3/2016 | Poole et al. |
| 2016/0069975 A1 | 3/2016 | Rothberg et al. |
| 2016/0128592 A1 | 5/2016 | Rosen et al. |
| 2016/0131727 A1 | 5/2016 | Sacolick et al. |
| 2016/0169992 A1 | 6/2016 | Rothberg et al. |
| 2016/0169993 A1 | 6/2016 | Rearick et al. |
| 2016/0223631 A1 | 8/2016 | Poole et al. |
| 2016/0231399 A1 | 8/2016 | Rothberg et al. |
| 2016/0231402 A1 | 8/2016 | Rothberg et al. |
| 2016/0231403 A1 | 8/2016 | Rothberg et al. |
| 2016/0231404 A1 | 8/2016 | Rothberg et al. |
| 2016/0299203 A1 | 10/2016 | Mileski et al. |
| 2016/0334479 A1 | 11/2016 | Poole et al. |
| 2017/0032877 A1 | 2/2017 | Inoue et al. |
| 2017/0102443 A1 | 4/2017 | Rearick et al. |
| 2017/0227616 A1 | 8/2017 | Poole et al. |
| 2017/0276747 A1 | 9/2017 | Hugon et al. |
| 2017/0276749 A1 | 9/2017 | Hugon et al. |
| 2018/0024208 A1 | 1/2018 | Rothberg et al. |
| 2018/0038931 A1 | 2/2018 | Rearick et al. |
| 2018/0088193 A1 | 3/2018 | Rearick et al. |
| 2018/0143274 A1 | 5/2018 | Poole et al. |
| 2018/0143275 A1 | 5/2018 | Sofka et al. |
| 2018/0143280 A1 | 5/2018 | Dyvorne et al. |
| 2018/0143281 A1 | 5/2018 | Sofka et al. |
| 2018/0144467 A1 | 5/2018 | Sofka et al. |
| 2018/0156881 A1 | 6/2018 | Poole et al. |
| 2018/0164390 A1 | 6/2018 | Poole et al. |
| 2018/0168527 A1 | 6/2018 | Poole et al. |
| 2018/0210047 A1 | 7/2018 | Poole et al. |
| 2018/0224512 A1 | 8/2018 | Poole et al. |
| 2018/0226190 A1 | 8/2018 | Meinke et al. |
| 2018/0238978 A1 | 8/2018 | McNulty et al. |
| 2018/0238980 A1 | 8/2018 | Poole et al. |
| 2018/0238981 A1 | 8/2018 | Poole et al. |
| 2019/0004130 A1 | 1/2019 | Poole et al. |
| 2019/0011510 A1 | 1/2019 | Hugon et al. |
| 2019/0011513 A1 | 1/2019 | Poole et al. |
| 2019/0011514 A1 | 1/2019 | Poole et al. |
| 2019/0011521 A1 | 1/2019 | Sofka et al. |
| 2019/0018094 A1 | 1/2019 | Mileski et al. |
| 2019/0018095 A1 | 1/2019 | Mileski et al. |
| 2019/0018096 A1 | 1/2019 | Poole et al. |
| 2019/0025389 A1 | 1/2019 | McNulty et al. |
| 2019/0033402 A1 | 1/2019 | McNulty et al. |
| 2019/0033414 A1 | 1/2019 | Sofka et al. |
| 2019/0033415 A1 | 1/2019 | Sofka et al. |
| 2019/0033416 A1 | 1/2019 | Rothberg et al. |
| 2019/0038233 A1 | 2/2019 | Poole et al. |
| 2019/0086497 A1 | 3/2019 | Rearick et al. |
| 2019/0101607 A1 | 4/2019 | Rothberg et al. |
| 2019/0122818 A1 | 4/2019 | Meinke et al. |
| 2019/0162806 A1 | 5/2019 | Poole et al. |
| 2019/0178962 A1 | 6/2019 | Poole et al. |
| 2019/0178963 A1 | 6/2019 | Poole et al. |
| 2019/0227136 A1 | 7/2019 | Mileski et al. |
| 2019/0227137 A1 | 7/2019 | Mileski et al. |
| 2019/0250227 A1 | 8/2019 | McNulty et al. |
| 2019/0250228 A1 | 8/2019 | McNulty et al. |
| 2019/0257903 A1 | 8/2019 | Poole et al. |
| 2019/0324098 A1 | 10/2019 | McNulty et al. |
| 2019/0353720 A1 | 11/2019 | Dyvorne et al. |
| 2019/0353723 A1 | 11/2019 | Dyvorne et al. |
| 2019/0353726 A1 | 11/2019 | Poole et al. |
| 2019/0353727 A1 | 11/2019 | Dyvorne et al. |

(56) References Cited

U.S. PATENT DOCUMENTS

| | | |
|---|---|---|
| 2020/0011952 A1 | 1/2020 | Rothberg et al. |
| 2020/0018806 A1 | 1/2020 | Rothberg et al. |
| 2020/0022611 A1 | 1/2020 | Nelson et al. |
| 2020/0022612 A1 | 1/2020 | McNulty et al. |
| 2020/0022613 A1 | 1/2020 | Nelson et al. |
| 2020/0025846 A1 | 1/2020 | Nelson et al. |
| 2020/0025851 A1 | 1/2020 | Rearick et al. |
| 2020/0033431 A1 | 1/2020 | Schlemper et al. |
| 2020/0034998 A1 | 1/2020 | Schlemper et al. |
| 2020/0041588 A1 | 2/2020 | O'Halloran et al. |
| 2020/0045112 A1 | 2/2020 | Sacolick et al. |
| 2020/0054241 A1 | 2/2020 | Nelson et al. |
| 2020/0058106 A1 | 2/2020 | Lazarus et al. |
| 2020/0064427 A1 | 2/2020 | Poole et al. |
| 2020/0200844 A1 | 6/2020 | Boskamp et al. |
| 2020/0209334 A1 | 7/2020 | O'Halloran et al. |
| 2020/0237310 A1 | 7/2020 | Lozano-Buhl et al. |
| 2020/0289019 A1 | 9/2020 | Schlemper et al. |
| 2020/0289022 A1 | 9/2020 | Coumans et al. |
| 2020/0294229 A1 | 9/2020 | Schlemper et al. |
| 2020/0294282 A1 | 9/2020 | Schlemper et al. |
| 2020/0294287 A1 | 9/2020 | Schlemper et al. |
| 2020/0337587 A1 | 10/2020 | Sacolick et al. |
| 2020/0355765 A1 | 11/2020 | Chen et al. |
| 2021/0173024 A1 | 6/2021 | Hugon |
| 2021/0173025 A1 | 6/2021 | Hugon |
| 2021/0173026 A1 | 6/2021 | Hugon et al. |
| 2021/0173027 A1 | 6/2021 | Hugon et al. |
| 2021/0173029 A1 | 6/2021 | Hugon |
| 2022/0082643 A1 | 3/2022 | Poole et al. |

FOREIGN PATENT DOCUMENTS

| | | |
|---|---|---|
| EP | 0801314 A1 | 10/1997 |
| EP | 1 004 888 A1 | 5/2000 |
| EP | 1004888 A1 | 5/2000 |
| EP | 1 069 575 A1 | 1/2001 |
| EP | 1069575 A1 | 1/2001 |
| JP | S63-143045 A | 6/1988 |
| JP | H04-82536 A | 1/2001 |
| WO | WO-2017/072805 A1 | 5/2017 |
| WO | WO-2017/134635 A1 | 8/2017 |
| WO | WO-2020/050776 A1 | 3/2020 |
| WO | WO-2020/109895 A1 | 6/2020 |

OTHER PUBLICATIONS

U.S. Appl. No. 17/116,237, filed Dec. 9, 2020, Hugon.
U.S. Appl. No. 17/116,601, filed Dec. 9, 2020, Hugon et al.
U.S. Appl. No. 17/116,680, filed Dec. 9, 2020, Hugon.
U.S. Appl. No. 29/716,483, filed Dec. 10, 2019, Hugon.
U.S. Appl. No. 29/716,476, filed Dec. 10, 2019, Hugon.
PCT/US2020/063906, Mar. 18, 2021, Invitation to Pay Additional Fees.
PCT/US2020/063906, May 11, 2021, International Search Report and Written Opinion.
PCT/US2020/063906, Jun. 23, 2022, International Preliminary Report on Patentability.
Invitation to Pay Additional Fees for International Application No. PCT/US2020/063906 dated Mar. 18, 2021.
International Search Report and Written Opinion for International Application No. PCT/US2020/063906 dated May 11, 2021.
International Preliminary Report on Patentability for International Application No. PCT/US2020/063906 dated Jun. 23, 2022.
U.S. Appl. No. 17/116,540, filed Dec. 9, 2020, Hugon et al.
U.S. Appl. No. 29/716,476, filed Dec. 10, 2019, Cedric Hugon.
U.S. Appl. No. 29/716,483, filed Dec. 10, 2019, Cedric Hugon.
Chandrana et al., Automatic alignment of multiple magnets into Halbach cylinders, Journal of Magnetism and Magnetic Materials 381, pp. 396-400, 2015 (Year: 2015).
Cooley et al., Design of sparse Halbach magnet arrays for portable MRI using a genetic algorithm. IEEE transactions on magnetics. Jan. 1, 2018;54(1):1-12.
Cooley et al., Two-dimensional imaging in a lightweight portable MRI scanner without gradient coils. Magnetic Resonance in Medicine. 2014. 12 pages.
Halbach, Design of permanent multi pole magnets with oriented rare earth cobalt material, Nuclear instruments and methods. Feb. 1, 1980; 169(1 ): 1-0.
Huang et al., Portable Low-cost MRI System based on Permanent Magnets/Magnet Arrays.arXiv preprint arXiv:1812.10474. Dec. 24, 2018. 30 pages.
International Preliminary Report on Patentability for International Application No. PCT/US2020/063933 dated Jun. 23, 2022.
International Preliminary Report on Patentability for International Application No. PCT/US2020/063980 dated Jun. 23, 2022.
International Search Report and Written Opinion for International Application No. PCT/US2020/063933 dated May 25, 2021.
International Search Report and Written Opinion for International Application No. PCT/US2020/063980 dated Jun. 16, 2021.
Invitation to Pay Additional Fees for International Application No. PCT/US2020/063933 dated Apr. 1, 2021.
Invitation to Pay Additional Fees for International Application No. PCT/US2020/063980 dated Apr. 22, 2021.
Moresi et al., Miniature permanent magnet for table-top NMR. Concepts in Magnetic Resonance Part B: Magnetic Resonance Engineering: An Educational Journal. 2003;19(1):35-43.
Raich et al., Design and construction of a dipolar Halbach array with a homogeneous field from identical bar magnets: NMR Mandhalas. Concepts in Magnetic Resonance Part B: Magnetic Resonance Engineering: An Educational Journal. Oct. 2004;23(1): 16-25.
Ren et al., Design and optimization of a ring-pair permanent magnet array for head imaging in a low-field portable MRI system. IEEE Transactions on Magnetics. Nov. 12, 2018;55(1 ): 1-8.
Ren et al., Magnet array for a portable magnetic resonance imaging system. 2015 IEEE MTT-S 2015 International Microwave Workshop Series on RF and Wireless Technologies for Biomedical and Healthcare Applications (IMWS-BIO) Sep. 21, 2015:92-95.
Soltner et al., Dipolar Halbach magnet stacks made from identically shaped permanent magnets for magnetic resonance. Concepts in magnetic resonance part a. 2010 Jul;36(4):21 I-22.
Zhang et al., Design, construction and NMR testing of a 1 tesla Halbach Permanent Magnet for Magnetic Resonance. COMSOL Users Conference, Boston. 2005. 5 pages.
Zhu et al., Halbach permanent magnet machines and applications: a review. IEE Proceedings-Electric Power Applications. Jul. 6, 2001;148(4):299-308.
Cooley, Portable Low-Cost Magnetic Resonance Imaging, Doctoral Dissertation, Massachusetts Institute of Technology, 2014 (Year: 2014).
Z. H. Ren, W. C. Mu and S. Y. Huang, "Design and Optimization of a Ring-Pair Permanent Magnet Array for Head Imaging in a Low-Field Portable MRI System," in IEEE Transactions on Magnetics, vol. 55, No. 1, pp. 1-8, Jan. 2019 (Year: 2019).

* cited by examiner

FERROMAGNETIC FRAME FOR MAGNETIC RESONANCE IMAGING

CROSS REFERENCE TO RELATED APPLICATIONS

This application is a continuation application of, and claims priority under 35 U.S.C. § 120 to U.S. application Ser. No. 17/116,173, titled, "FERROMAGNETIC FRAME FOR MAGNETIC RESONANCE IMAGING," filed on Dec. 9, 2020, which claims priority under 35 U.S.C. § 119(e) to U.S. Provisional Patent Application Ser. No. 62/946,000, titled "FERROMAGNETIC FRAME FOR MAGNETIC RESONANCE IMAGING," filed on Dec. 10, 2019, each of which is incorporated by reference in its entirety herein.

BACKGROUND

Magnetic resonance imaging (MRI) provides an important imaging modality for numerous applications and is widely utilized in clinical and research settings to produce images of the inside of the human body. As a generality, MRI is based on detecting magnetic resonance (MR) signals, which are electromagnetic waves emitted by atoms in response to state changes resulting from applied electromagnetic fields. For example, nuclear magnetic resonance (NMR) techniques involve detecting MR signals emitted from the nuclei of excited atoms upon the re-alignment or relaxation of the nuclear spin of atoms in an object being imaged (e.g., atoms in the tissue of the human body). Detected MR signals may be processed to produce images, which in the context of medical applications, allows for the investigation of internal structures and/or biological processes within the body for diagnostic, therapeutic and/or research purposes.

SUMMARY

Some embodiments are directed to an apparatus for providing a $B_0$ magnetic field for a magnetic resonance imaging (MRI) system. The apparatus comprises: at least one permanent $B_0$ magnet to contribute a magnetic field to the $B_0$ magnetic field for the MRI system; and a ferromagnetic frame configured to capture and direct at least some of the magnetic field generated by the at least one permanent $B_0$ magnet. The frame comprises: a first post having a first end and a second end; a first multi-pronged member coupled to the first end; and a second multi-pronged member coupled to the second end, wherein the first and second multi-pronged members support the at least one permanent $B_0$ magnet.

Some embodiments are directed to a method, the method comprising: imaging a patient using a magnetic resonance imaging (MRI) system. The MRI system comprises: at least one permanent $B_0$ magnet to contribute a magnetic field to a $B_0$ magnetic field for the MRI system; and a ferromagnetic frame configured to capture and direct at least some of the magnetic field generated by the at least one permanent $B_0$ magnet. The ferromagnetic frame comprises: a first post having a first end and a second end; a first multi-pronged member coupled to the first end; and a second multi-pronged member coupled to the second end, wherein the first and second multi-pronged members support the at least one permanent $B_0$ magnet.

Some embodiments are directed to a frame for capturing and directing at least some of a $B_0$ magnetic field generated by a magnetic resonance imaging (MRI) system. The frame comprises a ferromagnetic frame configured to capture and direct at least some of the $B_0$ magnetic field generated by at least one permanent $B_0$ magnet. The ferromagnetic frame comprises: a first post having a first end and a second end; a first multi-pronged member coupled to the first end; and a second multi-pronged member coupled to the second end, wherein the first and second multi-pronged members support the at least one permanent $B_0$ magnet.

Some embodiments are directed to an apparatus for providing a $B_0$ magnetic field for a magnetic resonance imaging (MRI) system. The apparatus comprises: at least one permanent $B_0$ magnet to contribute a magnetic field to the $B_0$ magnetic field for the MRI system; and a ferromagnetic frame configured to capture and direct at least some of the magnetic field generated by the $B_0$ magnet. The frame comprises: a first plate configured to support the at least one permanent $B_0$ magnet; and a first post attached to the first plate using a first connection assembly, wherein the first connection assembly includes: a first connector that connects the first post and the first plate; and a second connector attached to the first connector.

Some embodiments are directed to a frame for capturing and directing at least some of a $B_0$ magnetic field generated by a magnetic resonance imaging (MRI) system. The frame comprises a ferromagnetic frame configured to capture and direct at least some of the $B_0$ magnetic field generated by at least one permanent $B_0$ magnet. The ferromagnetic frame comprises: a first post comprising a body portion, a first end, and a second end, each of the first end and the second end comprising a layered junction coupled to the body portion of the first post; and a first plate coupled to the first end of the first post, wherein the first plate supports the at least one permanent $B_0$ magnet.

BRIEF DESCRIPTION OF DRAWINGS

Various aspects and embodiments will be described with reference to the following figures. It should be appreciated that the figures are not necessarily drawn to scale. In the drawings, each identical or nearly identical component that is illustrated in various figures is represented by a like numeral. For purposes of clarity, not every component may be labeled in every drawing.

DETAILED DESCRIPTION

Figure 1:
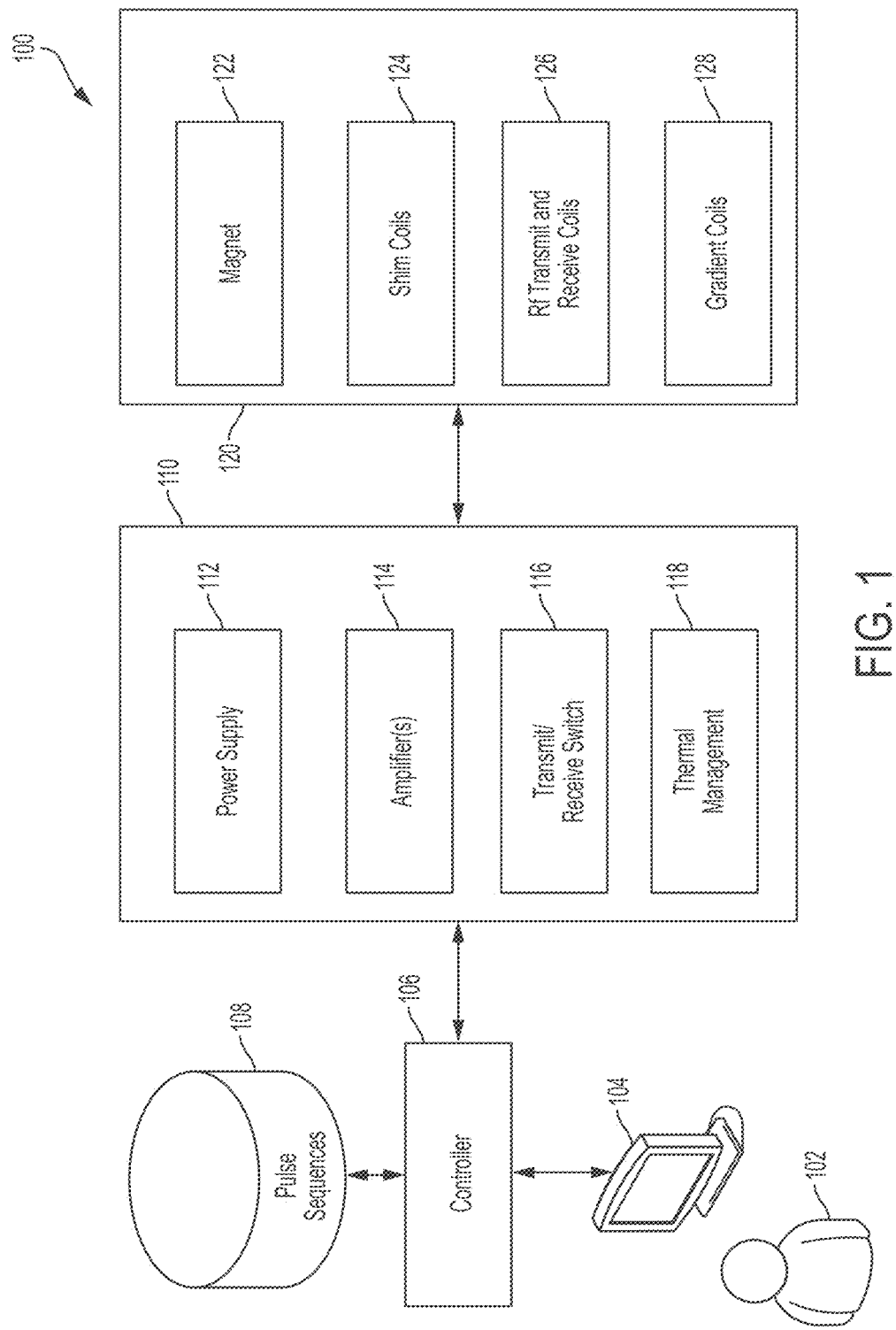
FIG. 1 illustrates exemplary components of an example magnetic resonance imaging (MRI) system, in accordance with some embodiments of the technology described herein.

Conventional magnetic resonance imaging (MRI) systems are overwhelmingly high-field systems, particularly for medical or clinical MRI applications. The general trend in medical imaging has been to produce MRI scanners with increasingly greater field strengths, with the vast majority of clinical MRI scanners operating at 1.5 T or 3 T, with higher field strengths of 7 T and 9 T used in research settings. As used herein, "high-field" refers generally to MRI systems presently in use in a clinical setting and, more particularly, to MRI systems operating with a main magnetic field (i.e., a $B_0$ field) at or above 1.5 T, though clinical systems operating between 0.5 T and 1.5 T are often also characterized as "high-field." By contrast, "low-field" refers generally to MRI systems operating with a $B_0$ field of less than or equal to approximately 0.2 T, though systems having a $B_0$ field of between 0.2 T and approximately 0.3 T have sometimes been characterized as low-field as a consequence of increased field strengths at the high end of the high-field regime.

Some low-field MRI systems increase accessibility to the imaging region by employing a magnet assembly having a C-shaped design. Such a design uses a C-shaped steel frame to support the magnetic components of the MRI system, with a single post connecting two halves of the MRI system with the imaging region located therebetween. Examples of such C-shaped designs are described in U.S. Pat. No. 10,353,030, titled "Low-Field Magnetic Resonance Imaging Methods and Apparatus", granted on Jul. 16, 2019, which is incorporated by reference herein in its entirety. However, the inventors have recognized that there are benefits (e.g., a reduced system weight and/or increased field efficiency) to using a design with additional supports.

Accordingly, the inventors have developed a lighter frame than a C-shaped design to support the $B_0$ magnets of an MRI system. In particular, the inventors have developed a forked frame, which reduces the weight of the total system by reducing the amount of material (e.g., steel) used to support the $B_0$ magnets as compared to a C-shaped design. In addition, the frame developed by the inventors reduces the conduction of eddy currents in the frame caused by the gradient fields, thereby increasing gradient field efficiency of the MRI system and improving image quality by reducing eddy current-related artefacts.

Another benefit of the forked frame design developed by the inventors is that the complexity of shimming may be reduced to achieve a desired degree of homogeneity of the main magnet field. The asymmetry of a C-shaped design induces an asymmetry in the $B_0$ magnetic field, which may be compensated by shimming to provide a suitably homogenous $B_0$ field in the imaging region of the MRI system. The symmetry of the forked frame design developed by the inventors may reduce the degree to which shimming must be performed, thereby simplifying the manufacturing process for an MRI system, which makes it quicker and cheaper.

The inventors have further appreciated that attaching blades to the forked frame can enhance the main magnetic field and the gradient magnetic fields of the MRI system. The blades can be sparsely arranged near the gradient coils to provide improved gradient field efficiency during imaging. Additionally, positioning the blades near the $B_0$ magnets can increase DC field efficiency by directing the magnetic flux toward the imaging region.

The inventors have developed an apparatus for providing a $B_0$ magnetic field for an MRI system. In some embodiments the apparatus may include at least one permanent $B_0$ magnet (e.g., a magnet comprising NdFeB, SmCo, AlNiCo, FeN, and/or other permanent magnet materials). The at least one permanent $B_0$ magnet may produce a magnetic field to contribute to the $B_0$ magnetic field. The apparatus may also include a ferromagnetic frame configured to capture and direct at least some of the magnetic field generated by the $B_0$ magnet. In some embodiments, the frame may include a first post with a first end and a second end, a first multi-pronged (e.g., forked) member coupled to the first end, and a second multi-pronged member coupled to the second end. The first and second multi-pronged members may support the at least one permanent $B_0$ magnet. In some embodiments, the apparatus may also include a second post having a third end and a fourth end. A third multi-pronged member may be coupled to the third end and a fourth multi-pronged member coupled to the fourth end.

In some embodiments, the first post, first multi-pronged member, and second multi-pronged member may each be formed of ferromagnetic material (e.g., steel, silicon steel, etc.). In some embodiments, the second post, third multi-pronged member, and fourth multi-pronged member each may also be formed of ferromagnetic material. Forming components of the frame out of a ferromagnetic material may direct magnetic flux of the $B_0$ magnet to increase field homogeneity and/or increase the $B_0$ magnetic field strength within the imaging region of the MRI system.

In some embodiments, the first multi-pronged member may include a stem and two prongs coupled to the stem. The two prongs may be spaced apart from one another by a gap. Each of the two prongs may be curved.

In some embodiments, the first multi-pronged member may be located opposite the third multi-pronged member. There may be a gap between the first and third multi-pronged member. In some embodiments, the second multi-pronged member may be located opposite the fourth multi-pronged member. There may be a gap between the second and the fourth multi-pronged member. The gaps may be air gaps, and may reduce eddy current conduction throughout the ferromagnetic frame.

In some embodiments, the at least one permanent $B_0$ magnet is a bi-planar magnet and may include first concentric permanent magnet rings and second concentric permanent magnet rings. The first and third multi-pronged members may support the first concentric permanent magnet rings, and the second and fourth multi-pronged members support the second concentric permanent magnet rings.

In some embodiments, the first and third multi-pronged members may be coupled to a first non-conductive component (e.g., a plastic component, a fiberglass component, etc.), and the first concentric permanent magnet rings may be arranged on a surface of the first non-conductive component. The second and fourth multi-pronged members may be coupled to a second non-conductive component, and the second concentric permanent magnet rings may be arranged on a surface of the second non-conductive component. The first non-conductive component and the second non-conductive component may be substantially planar.

In some embodiments, the apparatus may also include a first plurality of ferromagnetic blades (e.g., manufactured from steel, silicon steel, etc.). The first plurality of ferromagnetic blades may be coupled to the first multi-pronged member or the third multi-pronged member at an end of each of the first plurality of ferromagnetic blades. The end of each of the first plurality of ferromagnetic blades may be placed within a slot formed within the first multi-pronged member or the third multi-pronged member. In some embodiments, the ferromagnetic blades in the first plurality of ferromagnetic blades are arranged to extend radially from a common center. The blades may not contact the common center.

In some embodiments, each of the ferromagnetic blades may have a constant height and/or width along its length. Alternatively, in some embodiments, the height and/or width of each of the first plurality of ferromagnetic blades may vary along its length. For example, in some embodiments, the height and/or width of a ferromagnetic blade may be tapered. In some embodiments, the first plurality of blades includes at least 16 blades and at most 24 blades. Alternatively, in some embodiments, the first plurality of blades includes between 8 and 32 blades.

In some embodiments, the apparatus may include a second plurality of ferromagnetic blades. The second plurality of ferromagnetic blades may be coupled to the second multi-pronged member or the fourth multi-pronged member at an end of each of the second plurality of ferromagnetic blades. The end of each of the second plurality of ferromagnetic blades may be placed within a slot formed within the second multi-pronged member or the fourth multi-pronged member.

In some embodiments, the first post and the second post may be arranged at an angle of 180° such that the at least one permanent $B_0$ magnet is located between the first post and the second post. Alternatively, the first post and the second post may be arranged at angle in a range from 100° to 180°. The first post and the second post may be arranged at an angle in a range from 120° to 145°. The first post and the second post may be arranged at an angle of 120°. Reducing the angle between the first post and the second post may provide more accessibility to one side of the imaging region while maintaining most of the advantages of the symmetric configuration of 180°.

The inventors have further developed a low-field MRI system. In some embodiments, the system includes an apparatus for providing a $B_0$ magnetic field for the MRI system. The apparatus may include at least one permanent $B_0$ magnet to produce a magnetic field to contribute to the $B_0$ magnetic field. The apparatus may also include a ferromagnetic frame configured to capture and direct at least some of the magnetic field generated by the $B_0$ magnet. In some embodiments, the frame may include a first post with a first end and a second end, a first multi-pronged member (e.g., a forked member) coupled to the first end, and a second multi-pronged member coupled to the second end. The first and second multi-pronged members may support the at least one permanent $B_0$ magnet. In some embodiments the MRI system may include gradient coils configured to generate magnetic fields to provide spatial encoding of magnetic resonance (MR) signals, a radio frequency transmit coil, and a power system. The power system may be configured to provide power to the gradient coils and/or the radio frequency transmit coil. In some embodiments, the MRI system may be used to capture at least one MR image.

In some embodiments, a low-field MRI system comprising a ferromagnetic frame with one or more multi-pronged members, in accordance with embodiments described herein, may be used for imaging a patient.

The inventors have appreciated that lighter-weight, less complex, and better-performing forked frame designs may be attained by attaching some or all of the ferromagnetic components to non-ferromagnetic components. Thus, the inventors have developed frame designs in which ferromagnetic blades (e.g., 2 to 8 blades) are attached to a substantially planar non-ferromagnetic component rather than being fitted into slots machined in the forked frame. In this way, assembly and manufacture may be simplified. Additionally, the ferromagnetic blades may be positioned parallel to one of the x- or y-gradient magnetic fields, rather than radially, which improves gradient field efficiency.

In some embodiments, such forked-frame designs may include connectors extending between and securing the first post to the second post in a direction perpendicular to the ferromagnetic blades, thus improving structural rigidity and providing additional gradient efficiency to the x- and/or y-gradient magnetic field. For example, in some embodiments the connectors comprise ferromagnetic bars extending between the first post and the second post. The ferromagnetic blades are positioned to extend along a direction substantially perpendicular to the length of the ferromagnetic bars.

In some embodiments, the ferromagnetic bars are formed as a first and a second bar. The first and the second bar are positioned substantially parallel to one another. In some embodiments, a portion of the first bar is separated from a portion of the second bar by a gap. The gap has a width that is less than a quarter of the spacing between the first multi-pronged member and the third multi-pronged member. Alternatively or additionally, the gap has a width in a range from 75 mm to 100 mm.

The inventors have appreciated that manufacturing complexity of the frame may be reduced by forming the ferromagnetic frame out of multiple, layered components. For example, if the frame is constructed as a single piece, the machining of the piece may be more complex than if the frame is constructed from a number of smaller components (e.g., that may be cut from sheet metal stock or smaller blocks of material). Additionally, insulation layers may be inserted between the components of the frame to reduce eddy current circulation during operation of the resulting MRI system.

Accordingly, the inventors have developed an apparatus for providing a $B_0$ magnetic field for a magnetic resonance imaging (MRI) system, the apparatus including at least one permanent $B_0$ magnet to contribute a magnetic field to the $B_0$ magnetic field for the MRI system and a ferromagnetic frame configured to capture and direct at least some of the magnetic field generated by the $B_0$ magnet. The frame includes a first plate configured to support the at least one permanent $B_0$ magnet and a first post attached to the first plate using a first connection assembly. The first connection assembly includes a first connector that connects the first post and the first plate to one another, and a second connector attached to the first connector. In some embodiments, the second connector may be configured to provide additional enhancement of magnetic flux within the apparatus.

In some embodiments, the ferromagnetic frame also includes a second post attached to the first plate using a second connection assembly. The second connection assembly includes a third connector that connects the second post and the first plate, and a fourth connector attached to the third connector.

In some embodiments, the ferromagnetic frame also includes a second plate disposed opposite the first plate and configured to support the at least one permanent $B_0$ magnet. The second plate is attached to the first post using a third connection assembly and to the second post using a fourth connection assembly. The third connection assembly includes a fifth connector that connects the first post to the second plate and a sixth connector attached to the fifth connector. The fourth connection assembly includes a seventh connector that connects the second post to the second plate and an eighth connector attached to the seventh connector.

In some embodiments, the first connector comprises a ferromagnetic plate. For example, in some embodiments, the first connector comprises silicon steel. In some embodiments, the first connect is secured to the first post and the first plate using multiple fasteners.

In some embodiments, the second connector is secured to the first post by multiple fasteners. The multiple fasteners may pass through the first connector and enter the first post to secure the second connector to the first post.

In some embodiments, the ferromagnetic frame also includes at least one permanent magnet coupled to an interior face of the first post to provide additional and/or alternative homogenization of the $B_0$ magnetic field. The at least one permanent magnet, in some embodiments, comprises a cylindrical permanent magnet.

In some embodiments, the at least one permanent magnet comprises a first permanent magnet and a second permanent magnet. The first permanent magnet and the second permanent magnet are disposed along the length of the first post. In some embodiments, the first permanent magnet has a first polarization and the second permanent magnet has a second polarization opposite the first polarization. For example, in some embodiments, one of the first and second polarizations is directed toward the interior face of the first post.

Following below are more detailed descriptions of various concepts related to, and embodiments of, ferromagnetic frames for MRI. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

FIG. 1 is a block diagram of components of a MRI system 100. In the illustrative example of FIG. 1, MRI system 100 comprises computing device 104, controller 106, pulse sequences store 108, power management system 110, and magnetics components 120. It should be appreciated that system 100 is illustrative and that an MRI system may have one or more other components of any suitable type in addition to or instead of the components illustrated in FIG. 1. However, a MRI system will generally include these high level components, though the implementation of these components for a particular MRI system may differ.

As illustrated in FIG. 1, magnetics components 120 comprise $B_0$ magnet 122, shim coils 124, RF transmit and receive coils 126, and gradient coils 128. Magnet 122 may be used to generate the main magnetic field $B_0$. Magnet 122 may be any suitable type or combination of magnetics components that can generate a desired main magnetic $B_0$ field. In some embodiments, magnet 122 may be a permanent magnet, an electromagnet, a superconducting magnet, or a hybrid magnet comprising one or more permanent magnets and one or more electromagnets and/or one or more superconducting magnets. In some embodiments, magnet 122 may be a bi-planar permanent magnet and, in some embodiments, ma include multiple sets of concentric permanent magnet rings.

Gradient coils 128 may be arranged to provide gradient fields and, for example, may be arranged to generate gradients in the $B_0$ field in three substantially orthogonal directions (X, Y, Z). Gradient coils 128 may be configured to encode emitted MR signals by systematically varying the $B_0$ field (the $B_0$ field generated by magnet 122 and/or shim coils 124) to encode the spatial location of received MR signals as a function of frequency or phase. For example, gradient coils 128 may be configured to vary frequency or phase as a linear function of spatial location along a particular direction, although more complex spatial encoding profiles may also be provided by using nonlinear gradient coils.

MRI is performed by exciting and detecting emitted MR signals using transmit and receive coils, respectively (often referred to as radio frequency (RF) coils). Transmit/receive coils may include separate coils for transmitting and receiving, multiple coils for transmitting and/or receiving, or the same coils for transmitting and receiving. Thus, a transmit/receive component may include one or more coils for transmitting, one or more coils for receiving and/or one or more coils for transmitting and receiving. Transmit/receive coils are also often referred to as Tx/Rx or Tx/Rx coils to generically refer to the various configurations for the transmit and receive magnetics component of an MRI system. These terms are used interchangeably herein. In FIG. 1, RF transmit and receive coils 126 comprise one or more transmit coils that may be used to generate RF pulses to induce an oscillating magnetic field $B_1$. The transmit coil(s) may be configured to generate any suitable types of RF pulses.

Power management system 110 includes electronics to provide operating power to one or more components of the low-field MRI system 100. For example, power management system 110 may include one or more power supplies, gradient power components, transmit coil components, and/or any other suitable power electronics needed to provide suitable operating power to energize and operate components of MRI system 100. As illustrated in FIG. 1, power management system 110 comprises power supply 112, power component(s) 114, transmit/receive switch 116, and thermal management components 118 (e.g., cryogenic cooling equipment for superconducting magnets). Power supply 112 includes electronics to provide operating power to magnetic components 120 of the MRI system 100. For example, power supply 112 may include electronics to provide operating power to one or more $B_0$ coils (e.g., $B_0$ magnet 122) to produce the main magnetic field for the low-field MRI system. Transmit/receive switch 116 may be used to select whether RF transmit coils or RF receive coils are being operated.

Power component(s) 114 may include one or more RF receive (Rx) pre-amplifiers that amplify MR signals detected by one or more RF receive coils (e.g., coils 126), one or more RF transmit (Tx) power components configured to provide power to one or more RF transmit coils (e.g., coils 126), one or more gradient power components configured to provide power to one or more gradient coils (e.g., gradient coils 128), and one or more shim power components configured to provide power to one or more shim coils (e.g., shim coils 124).

As illustrated in FIG. 1, MRI system 100 includes controller 106 (also referred to as a console) having control electronics to send instructions to and receive information from power management system 110. Controller 106 may be configured to implement one or more pulse sequences, which are used to determine the instructions sent to power management system 110 to operate the magnetic components 120 in a desired sequence (e.g., parameters for operating the RF transmit and receive coils 126, parameters for operating gradient coils 128, etc.). As illustrated in FIG. 1, controller 106 also interacts with computing device 104 programmed to process received MR data. For example, computing device 104 may process received MR data to generate one or more MR images using any suitable image reconstruction process(es). Controller 106 may provide information about one or more pulse sequences to computing device 104 for the processing of data by the computing device. For example, controller 106 may provide information about one or more pulse sequences to computing device 104 and the computing device may perform an image reconstruction process based, at least in part, on the provided information.

Figure 2:
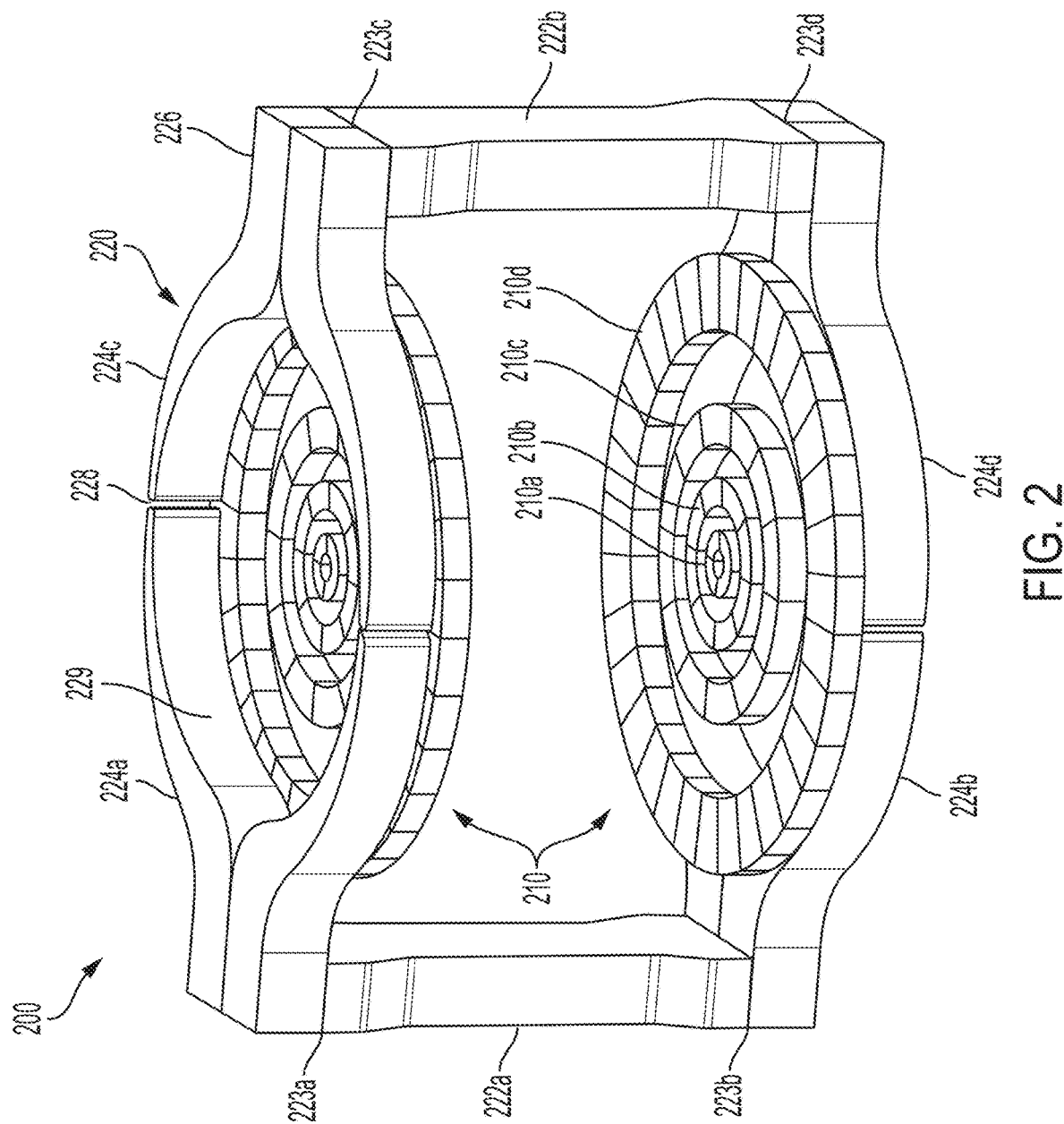
FIG. 2 illustrates an exemplary embodiment of an apparatus for providing a $B_0$ magnetic field for an MRI system, in accordance with some embodiments of the technology described herein.

FIG. 2 depicts a schematic of an apparatus 200 for providing a $B_0$ magnetic field for an MRI system, in accordance with some embodiments of the technology described herein. The apparatus 200 may include $B_0$ magnets 210 and a frame 220 that captures electromagnetic flux produced by the $B_0$ magnet 210 and transfers the flux to the opposing permanent magnet to increase the flux density between $B_0$ magnets 210. The $B_0$ magnets 210 may be arranged in a bi-planar geometry and may each include, for example, a plurality of concentric permanent magnet rings 210a-d as depicted in FIG. 2. In particular, as visible in FIG. 2, $B_0$ magnet 210 comprises a lower portion having a first set of concentric permanent magnet rings including: an inner ring of permanent magnets 210a, a first middle ring of permanent magnets 210b, a second middle ring of permanent magnets 210c, and an outer ring of permanent magnets 210d. The upper portion of $B_0$ magnet 210 includes another set of concentric permanent magnet rings. In other embodiments, the $B_0$ magnets 210 may, additionally or alternatively, include electromagnets, superconducting magnets, other permanent magnets, or any suitable combinations thereof.

The permanent magnet material used may be selected depending on the design requirements of the system. For example, according to some embodiments, the permanent magnets (or some portion thereof) may be made of NdFeB, which produces a magnetic field with a relatively high magnetic field per unit volume of material once magnetized. According to some embodiments, SmCo material is used to form the permanent magnets, or some portion thereof. While NdFeB produces higher field strengths (and in general is less expensive than SmCo), SmCo exhibits less thermal drift and thus provides a more stable magnetic field in the face of temperature fluctuations. Other types of permanent magnet material(s) may be used as well, as the aspects of the technology described herein are not limited in this respect. In general, the type or types of permanent magnet material utilized will depend, at least in part, on the field strength, temperature stability, weight, cost and/or ease of use requirements of a given $B_0$ magnet implementation.

The permanent magnet rings 210a-d may be sized and arranged to produce a homogenous field of a desired strength in the central region (e.g., the field of view and/or the imaging region) between permanent magnets 210. It may be appreciated that $B_0$ magnet 210 may include any suitable number of permanent magnet rings, not only four permanent magnet rings as depicted in FIG. 2. In some embodiments, such as pictured in exemplary FIG. 2, the permanent magnet rings 210a-d may be formed of a plurality of permanent magnet blocks. The dimensions (e.g., height, width) of the blocks may be varied to facilitate the production of a magnetic field of desired strength and homogeneity. For example, in some embodiments, the heights of the permanent magnet rings may increase away from the center of the magnet. For instance, in some embodiments, the height of permanent magnet ring 210b may be larger than that of permanent magnet 210a, the height of permanent magnet ring 210c may be larger than that of permanent magnet 210b, and the height of permanent magnet 210d may be larger than that of permanent magnet 210d. Aspects of varying heights and/or widths of concentric permanent magnet rings are further described in U.S. Pat. Pub. No.: 2019/0353726, titled "B0 Magnet Methods and Apparatus For A Magnetic Resonance Imaging System", filed on May 20, 2019, which is incorporated by reference herein in its entirety.

The apparatus 200 further includes frame 220 configured to capture magnetic flux generated by $B_0$ magnets 210 and direct it to the opposing side of the $B_0$ magnet to increase the magnetic flux density in between $B_0$ magnets 210, thereby increasing the field strength within the field of view of the $B_0$ magnet. By capturing magnetic flux and directing it to the region between $B_0$ magnets 210, less permanent magnet material can be used in $B_0$ magnets 210 to achieve a desired field strength, thus reducing the size, weight, and cost of the $B_0$ magnet. Alternatively, for given permanent magnets, the field strength can be increased, thus improving the signal-to-noise ratio (SNR) of the system without having to use increased amounts of permanent magnet material.

For exemplary apparatus 200, frame 220 includes a first post 222a and a second post 222b, the first post 222a having a first end 223a and a second end 223b and the second post 22b having a third end 223c and a fourth end 223d. Multi-pronged members 224a, 224b are coupled to the first end 223a and second end 223b of first post 222a and multi-pronged members 224c, 224d are coupled to the third end 223c and fourth end 223d of the second post 222b. Multi-pronged members 224a-d may be coupled to the first post 222a and second post 222b through stem members 226.

As shown in FIG. 2, first and second posts 222a,b may be positioned opposite each other at an angle of 180° such that $B_0$ magnets 210 are positioned between the first and second posts 222a,b. However, it may be appreciated that first and second posts 222a,b may be positioned at angles other than 180° (e.g., 120°) in order to increase accessibility to one side of the field of view of $B_0$ magnets 210 while retaining most of the advantages of the symmetry of the apparatus 200. For example, in some embodiments, first and second posts 222a,b may be positioned at any angle in a range from 100° to 180° (e.g., 120°, 135°, 150°, 165°, or 180°). Alternatively, in other embodiments, first and second posts 222a,b may be positioned at any angle in a range from 120° to 145°.

Multi-pronged members 224a-d may capture electromagnetic flux generated by $B_0$ magnets 210 and direct the electromagnetic flux to first and second posts 222a,b to be circulated via a magnetic return path of the frame. This electromagnetic flux capturing may increase the flux density in the field of view of the $B_0$ magnet, in accordance with some embodiments of the technology described herein. As shown in FIG. 2, multi-pronged members 224a-d includes two prongs with a collector area 229 disposed between the two prongs. However, in other embodiments, multi-pronged members 224a-d may include two or more prongs (e.g., 4 prongs, 6 prongs) to occupy the collector area 229 and increase capture of electromagnetic flux generated by $B_O$ magnets 210.

In some embodiments, frame 220, including multi-pronged members 224a-d and first and second posts 222a,b, may be constructed of any desired ferromagnetic material, for example, low carbon steel and/or CoFe, and/or silicon steel, etc. to provide the desired magnetic properties for the frame 220. In some embodiments, first and second posts 222a,b and/or multi-pronged members 224a-d may be constructed of laminated ferromagnetic material (e.g., any of the aforementioned ferromagnetic materials) in order to reduce persistent circulation of eddy currents around the cross-section of the multi-pronged members 224a-d. In such embodiments, first and second posts 222a,b and/or multi-pronged members 224a-d may be formed of laminations disposed in planes substantially orthogonal to the planes of $B_O$ magnets 210.

Figure 6A:
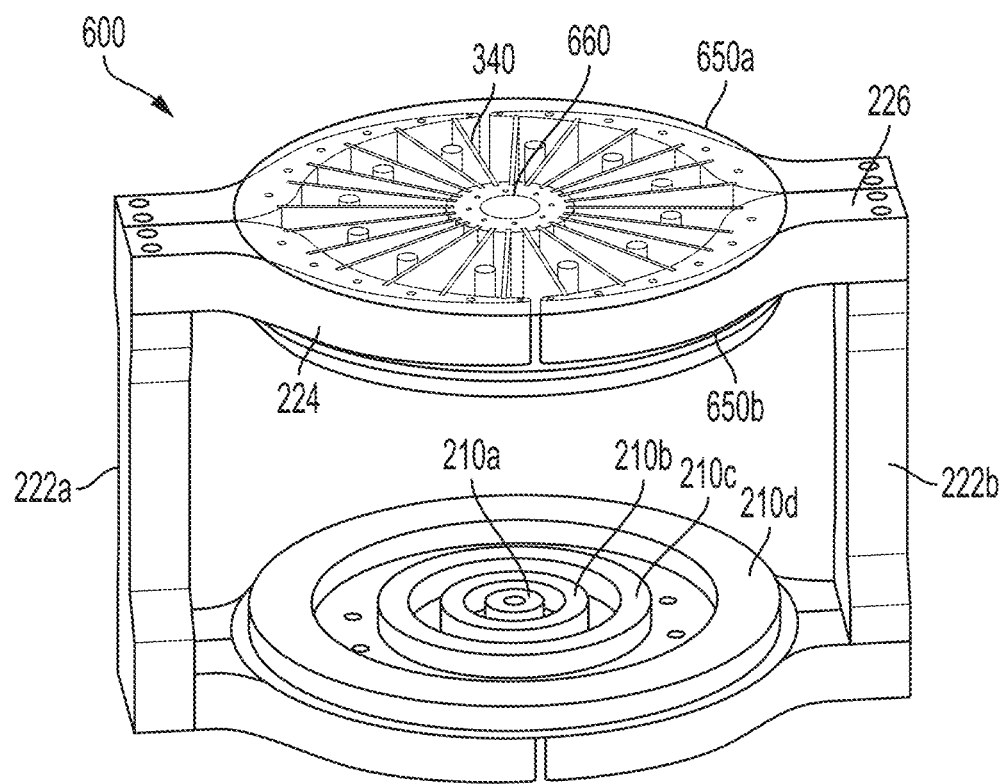
FIGS. 6A-6C illustrate views of an apparatus for providing a $B_0$ magnetic field for an MRI system and including non-conductive support structures, in accordance with some embodiments of the technology described herein.
Figure 6B:
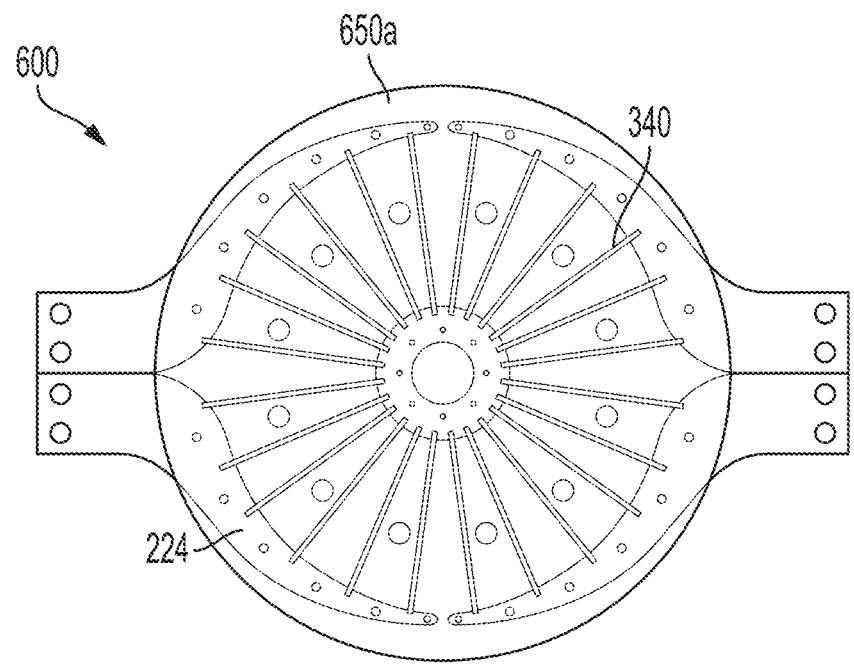
Figure 6C:
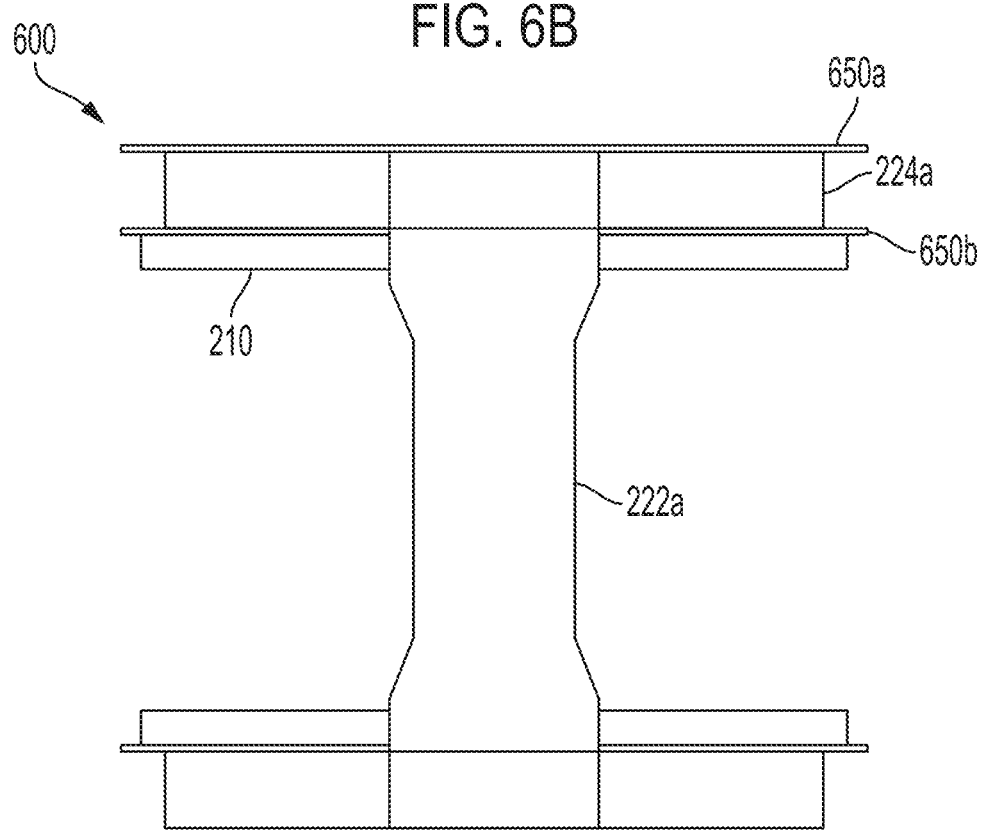

In some embodiments, multi-pronged members 224a-d may attach to non-conductive components (not pictured in FIG. 2) configured to support $B_O$ magnets 210, as described herein including with reference to FIGS. 6A-6C. Multi-pronged members 224a-d may be generally designed to reduce the amount of magnetic material needed to support the permanent magnets while still providing sufficient cross-section for the return path for the magnetic flux generated by $B_O$ magnets 210. Such a design may be as much as 20% lighter than a C-shaped frame (e.g., weighing between approximately 220 kg and 300 kg for a structure with an accessible gap of 35 cm and providing a $B_O$ magnetic field of 65 mT and a shimmed homogeneity of 500 ppm peak-to-peak over a 20 cm diameter sphere).

Additionally, because multi-pronged members 224a-d reduce the amount of magnetic material used in frame 220, multi-pronged members 224a-d also reduce the surface area available for eddy current conduction during operation of the gradient coils of the MRI system. This reduction may result in reduced time constants and increased overall gradient field efficiency of the MRI system.

Further, in some embodiments, multi-pronged members 224a-d may be arranged with a gap 228 between ends of opposing multi-pronged members 224a-d, as seen in exemplary FIG. 2. The gap 228 may be an air gap. Such an air gap may eliminate a conduction path across the direction between opposing posts 222. The gap 228 may accordingly further reduce eddy current conduction in the frame 220 during MR imaging.

As depicted in the example of FIG. 2, a collector area 229 (e.g., an open area over the $B_O$ magnets 210) may be located between multi-pronged members 224a-d. The collector area 229 may channel electromagnetic flux from the magnet rings into the first and second posts 222a,b. The collector area 229 may also provide enhancement to the gradient field by the inclusion of a number of conductive blades 340 as depicted in the example of FIG. 3.

Figure 3:
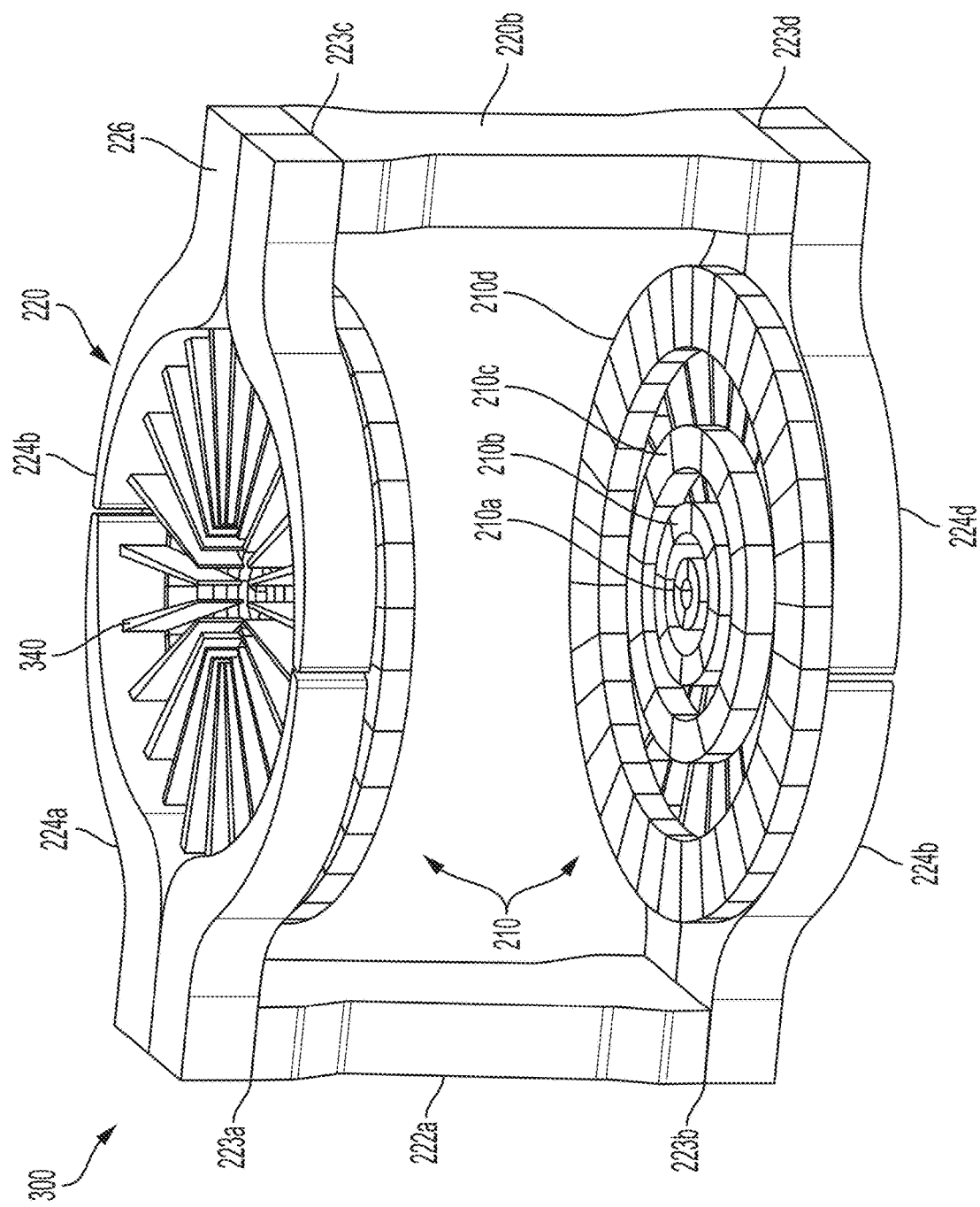
FIG. 3 illustrates an exemplary embodiment of an apparatus for providing a $B_0$ magnetic field for an MRI system, the assembly including radial blades, in accordance with some embodiments of the technology described herein.

FIG. 3 illustrates an embodiment of an apparatus 300 having blades 340 configured to enhance gradient magnetic fields generated by an MRI system that includes apparatus 330, in accordance with some embodiments of the technology described herein. Blades 340 may be arranged to cover the surface behind the gradient coils (not pictured) in a sparse manner, providing improved gradient field efficiency while minimizing eddy current conduction. The apparatus 300 may include a number of blades 340, such as 16 or 24 blades, to provide the improved gradient field efficiency. Alternatively, the apparatus 300 may include a number of blades 340 in a range from 16 to 24 blades, or in a range from 8 to 32 blades.

In some embodiments, the blades 340 may be arranged in a radial manner, extending towards a common center in the collection area 229 between multi-pronged members 224a-d. Blades 340 may not meet or touch the common center in order to prevent the formation of a conduction path for eddy currents between opposing blades 340. As a result, the eddy current time constants for exemplary apparatus 300 may be less than half the eddy current time constants for comparable C-shaped designs. Although not shown in FIG. 3, in some embodiments, the blades 340 may be coupled to one or more non-conductive elements at the common center of the collection area 229 for stability (e.g., the ends closer to the center may slide into plastic slots, as shown by non-conductive element 660 of FIG. 6A).

While blades 340 may increase the weight of apparatus 300, blades 340 also increase the collection of electromagnetic flux from $B_O$ magnets 210, thereby increasing DC-field efficiency, in accordance with some embodiments of the technology described herein. The increased DC-field efficiency provided by blades 340 may allow for a reduction in the weight of the permanent magnet material used in $B_O$ magnets 210, potentially reducing the overall raw materials cost of the apparatus 300.

In some embodiments, to provide improved gradient field efficiency, blades 340 may be formed of a ferromagnetic material. The blades may be formed of, for example, low carbon steel, CoFe, and/or silicon steel to provide the desired magnetic properties. The blades 340 may be formed of a same ferromagnetic material as frame 220, or may be formed of a different ferromagnetic material as frame 220.

In some embodiments, blades 340 may be formed separately from the multi-pronged members 224a-d. The blades may be coupled to multi-pronged members 224a-d by, for example, being inserted into machined slots (not pictured) in multi-pronged members 224a-d. In such embodiments, the blades 340 may be formed by, for example, stamping or laser cutting from sheet metal stock. Alternatively, blades 340 and multi-pronged members 224a-d may be cast together as a single piece to reduce the number of parts needed for assembly.

In some embodiments, the blades 340 may have specific dimensions in order to provide the desired magnetic properties. For example, the blades 340 may be tall enough to avoid magnetic saturation by the $B_O$ magnets 210 in order to provide enhancement to the gradient coils. However, the blades 340 may not be too tall, or they will provide additional surface area for eddy current conduction. For example, the blades 340 may be approximately half the height of the multi-pronged members 224a-d in order to provide these desired magnetic properties. Similarly, blades 340 may be thin in order to reduce eddy current conduction caused by the additional material. For example, in some embodiments the blades 340 may be approximately 5 mm in width. Alternatively, the blades 340 may be made thicker while the total number of blades 340 may be reduced in order to reduce assembly complexity.

Figure 4A:
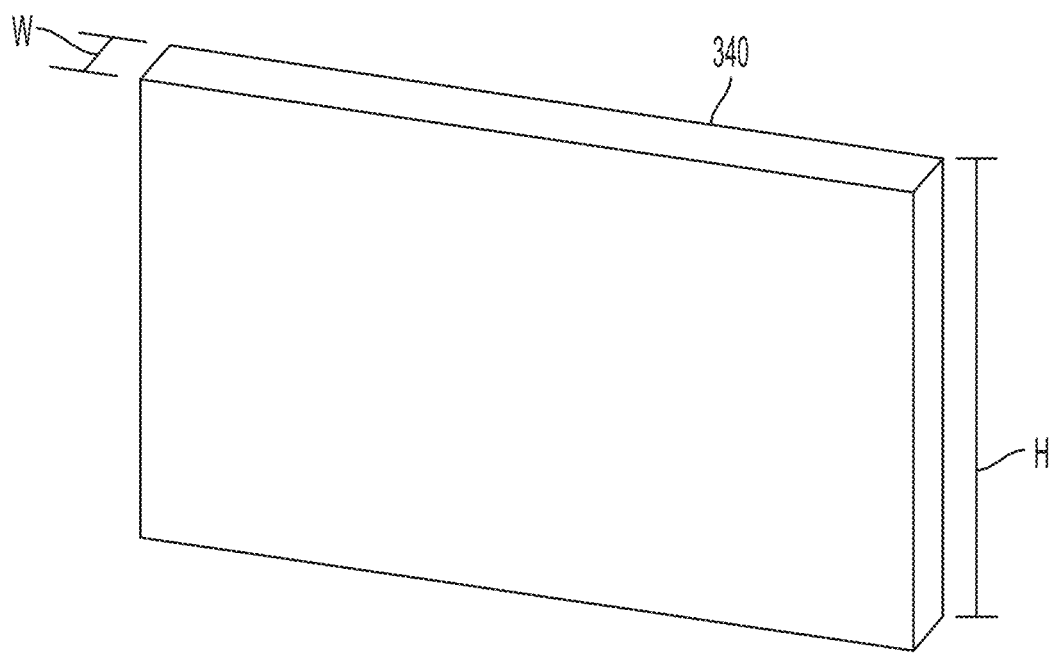
FIGS. 4A-4C illustrate different embodiments of blades used as part of the example apparatus shown in FIG. 3, in accordance with some embodiments of the technology described herein.
Figure 4B:
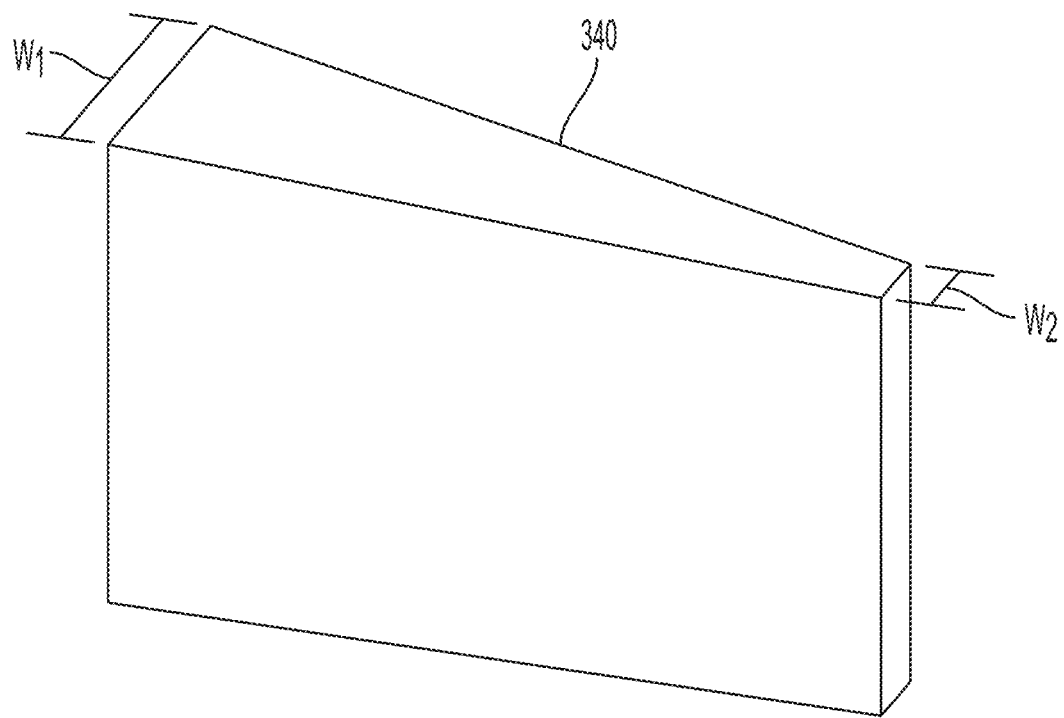
Figure 4C:
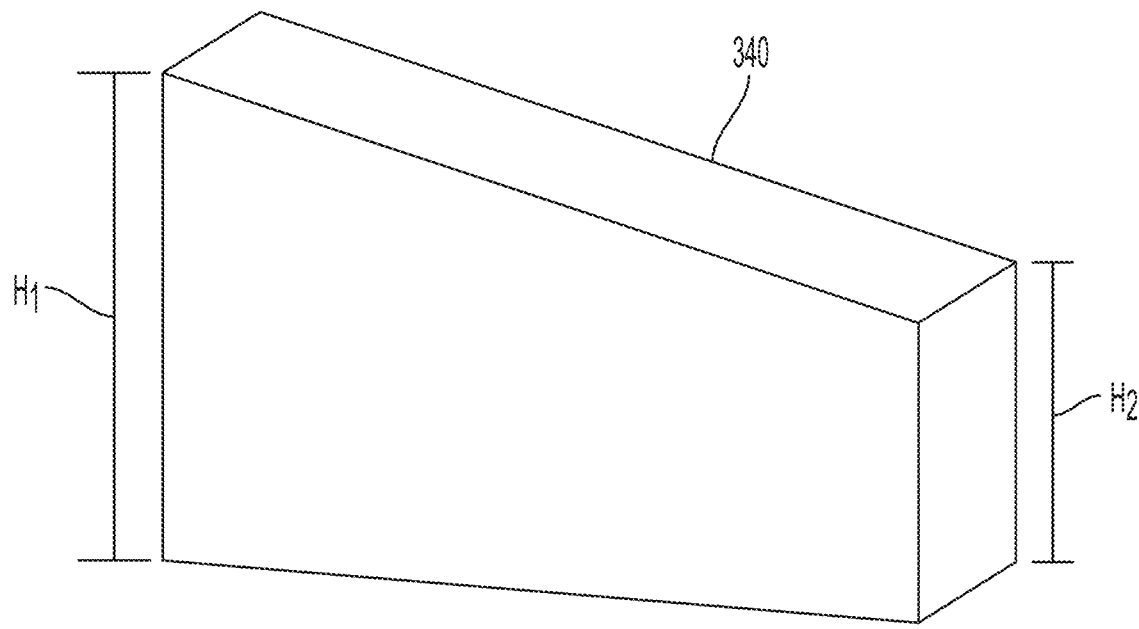

In some embodiments, blades 340 may have constant profiles along their lengths. In other embodiments, blades 340 may have tapered profiles along their lengths. Examples of such blade profiles are depicted in FIGS. 4A-4C. FIG. 4A shows an example of a blade 340 having a constant height H and a constant width W along its length, in accordance with some embodiments of the technology described herein.

FIG. 4B shows an example of a blade 340 having a tapered width, in accordance with some embodiments of the technology described herein. The width of blade 340 changes along the blade's length from a first width W1 at a first end to a second, smaller width W2 at a second end of the blade 340. The first end of the blade may be the end attached to multi-pronged members 224a-d of the apparatus 300 such that the second end is positioned near the common center of the collection area.

FIG. 4C shows an alternative example of a blade 340 having a tapered height, in accordance with some embodiments of the technology described herein. The height of blade 340 may change along the blade's length from a first height H1 at a first end to a second, smaller height H2 at a second end of the blade 340. The first end of the blade may be attached to multi-pronged members 224a-d of the apparatus 300 such that the second end is positioned near the common center of the collection area.

Figure 5:
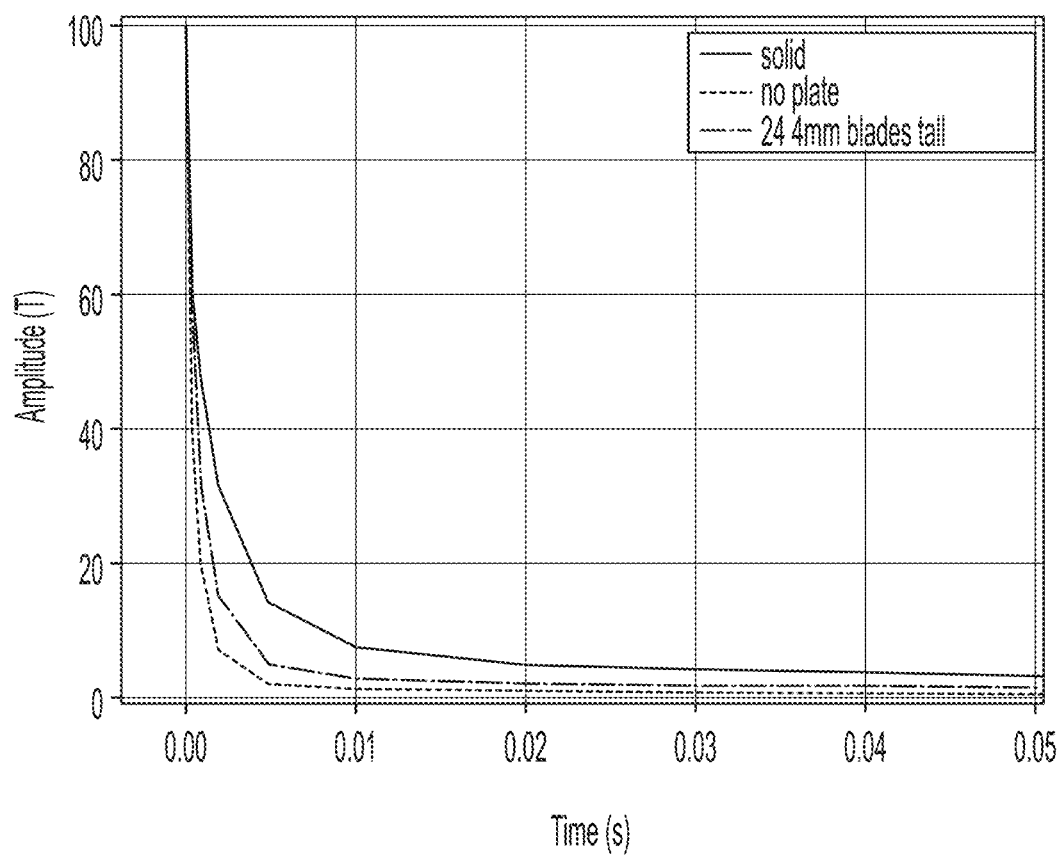
FIG. 5 illustrates simulated gradient field decay over time for different embodiments of an apparatus for providing a $B_0$ magnetic field for an MRI system, in accordance with some embodiments of the technology described herein.

FIG. 5 depicts simulated gradient field decay over time for different configurations of an apparatus for providing a $B_0$ magnetic field for an MRI system, in accordance with some embodiments of the technology described herein. At time equal to zero, a simulated gradient field along a single axis is quickly ramped down. The gradient field then decays at different rates depending on the structure near the gradient coils. The three curves, from top to bottom, show gradient field decay over time for an apparatus including solid plates supporting the $B_0$ magnets, an apparatus including blades (e.g., blades 340) arranged near the $B_0$ magnets, and an apparatus including empty space near the $B_0$ magnets (e.g., collection area 229 between prongs of multi-pronged members 224a-d, as described in FIG. 2). The blade configuration offers a faster gradient field decay than a more conventional solid plate configuration. The empty space configuration generates 12 mT/m at full current while the blade configuration generations 14.7 mT/m at full current. The solid plate provides 15.6 mT/m.

FIGS. 6A-6C depict different views of an apparatus 600 for providing a $B_0$ magnetic field for an MRI system, in accordance with some embodiments of the technology described herein. Apparatus 600 is similar to apparatus 300 of FIG. 3, but includes non-conductive support structures 650a and 650b above and below multi-pronged members 224a-d. Apparatus 600 also includes non-conductive element 660 coupled with central ends of blades 340. Non-conductive support structures 650a and 650b and/or non-conductive element 660 may be made of any suitable non-conductive material, including but not limited to plastic and/or fiberglass.

In some embodiments, non-conductive support structures 650a and 650b may be grooved to provide locations and support to the blades 340. Additionally, the non-conductive support structures 650a and 650b may protect the blades 340 from environmental damage (e.g., dust, dirt). The non-conductive support structure 650b may support the $B_0$ magnets 210, which may be mounted directly to a surfaces of the non-conductive support structure 650b. In some embodiments, such surfaces may be substantially planar.

Figure 7:
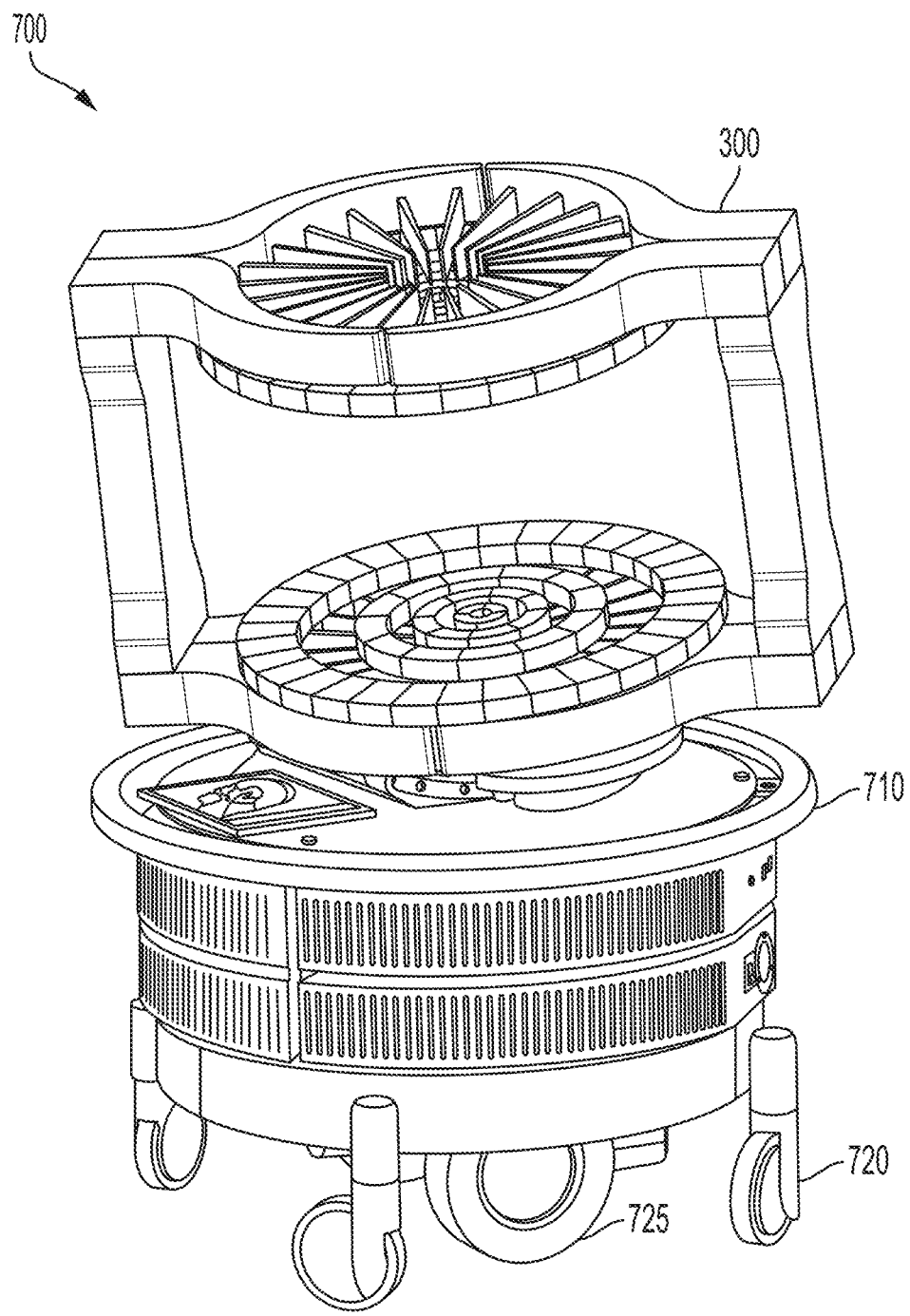
FIG. 7 illustrates a portable MRI system including the apparatus of FIG. 3, in accordance with some embodiments of the technology described herein.

Using the techniques described herein, the inventors have developed portable, low power MRI systems capable of being brought to the patient, providing affordable and widely deployable MRI where it is needed. FIG. 7 shows an example of a portable, low-field MRI system 700 including the apparatus 300 of FIG. 3, in accordance with some embodiments of the technology described herein. The apparatus 300 may be supported by a base 710. Base 710 may house the power components and/or electronics discussed in connection with FIG. 1, including power components configured to operate the MRI system 700.

Base 710 may also include one or more transport mechanisms 720 which enable point-of-care use of MRI system 700, in accordance with some embodiments of the technology described herein. In the example of FIG. 7, the transport mechanisms 720 are depicted as wheels, but other transport mechanisms may be used. In some embodiments, transport mechanisms 720 may include a motorized component 725 may be provided to allow the MRI system 700 to be driven from location to location, for example, using a control such as a joystick or other control mechanism provided on or remote from the MRI system 700. In this manner, MRI system 700 can be transported to the patient and maneuvered to the bedside to perform imaging, as illustrated in FIG. 8.

Figure 8:
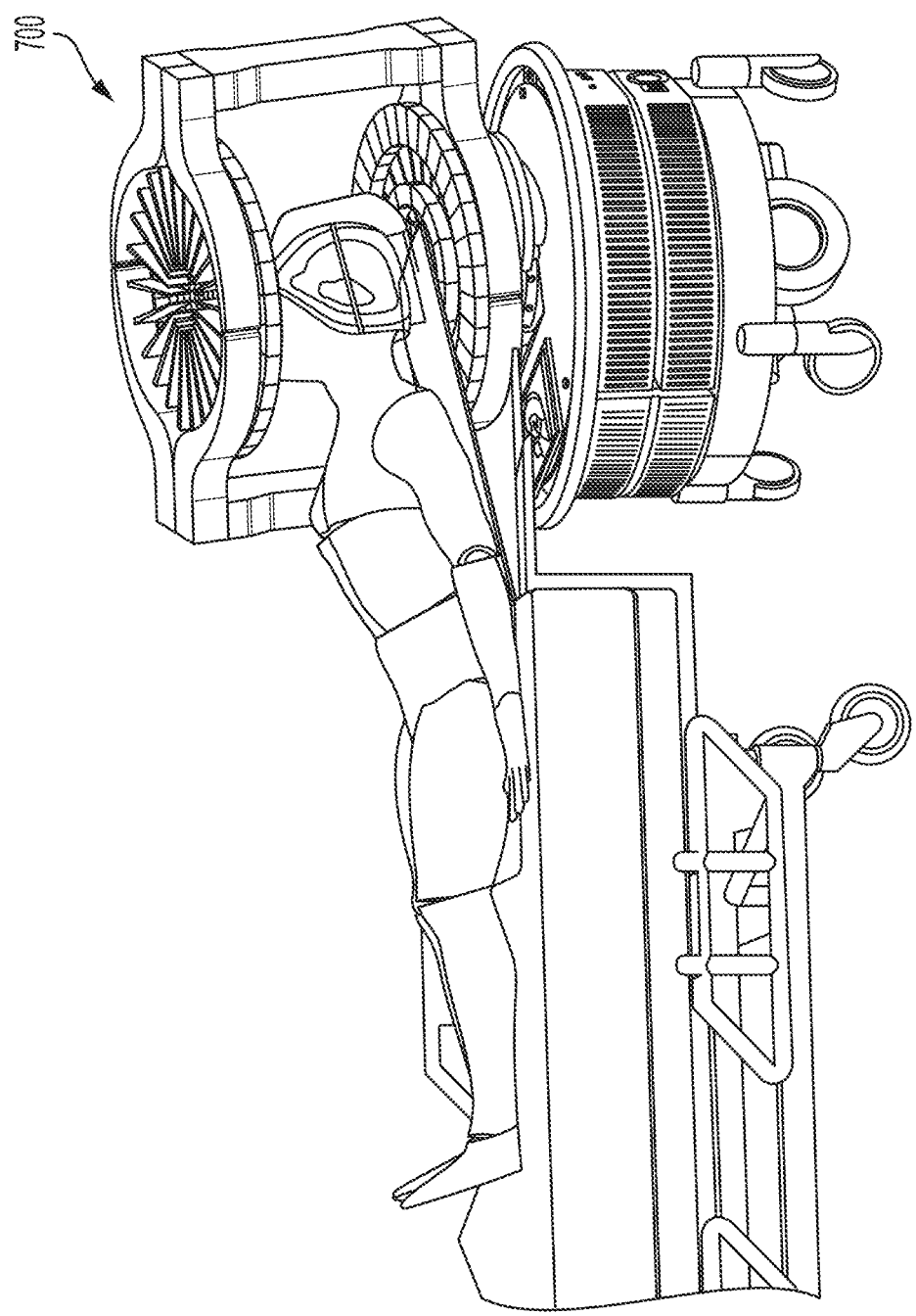
FIG. 8 illustrates the use of the portable MRI system of FIG. 7 to capture a magnetic resonance image of a patient's head, in accordance with some embodiments of the technology described herein.

FIG. 8 depicts the use of the portable MRI system of FIG. 7 to perform a brain scan of a patient, in accordance with some embodiments of the technology described herein. During the brain scan, the MRI system 700 may be used to capture at least one magnetic resonance image of the patient for clinical use.

Figure 9A:
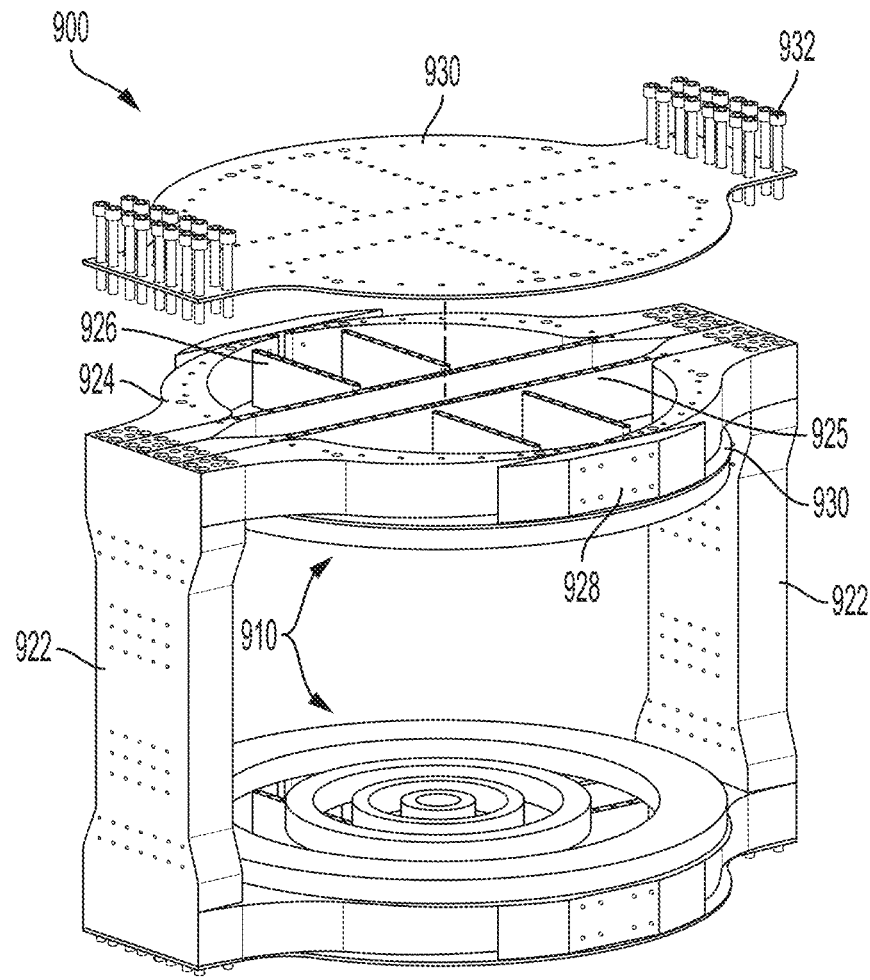
FIGS. 9A-9D illustrate views of an apparatus for providing a $B_0$ magnetic field for an MRI system, the assembly including ferromagnetic connectors and blades, in accordance with some embodiments of the technology described herein.
Figure 9B:
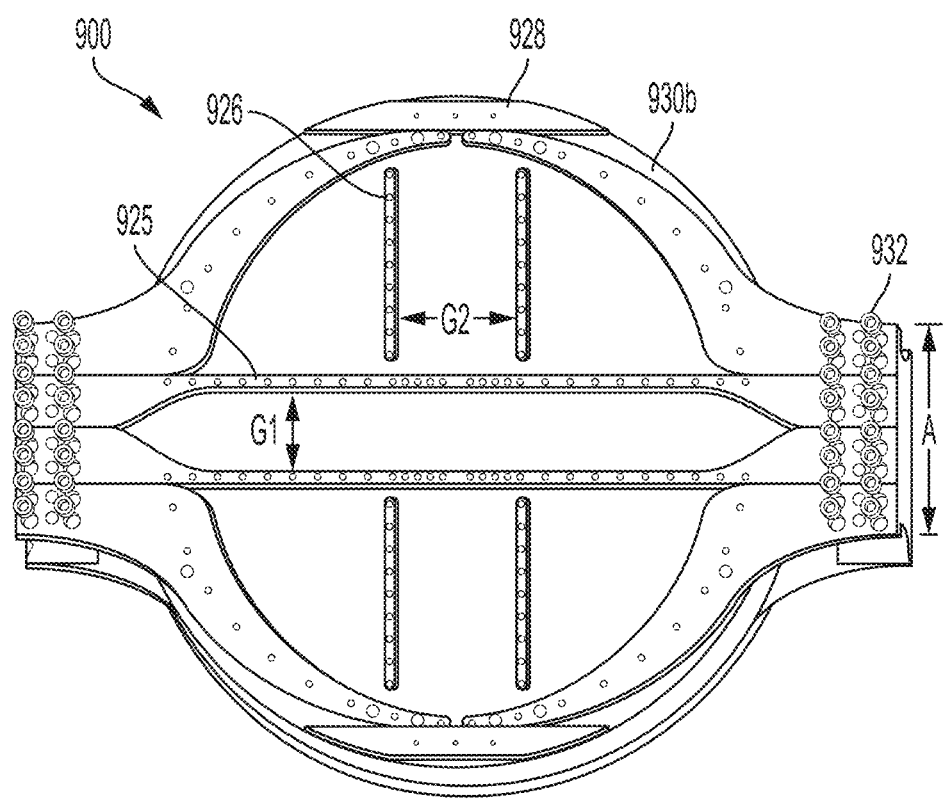
Figure 9C:
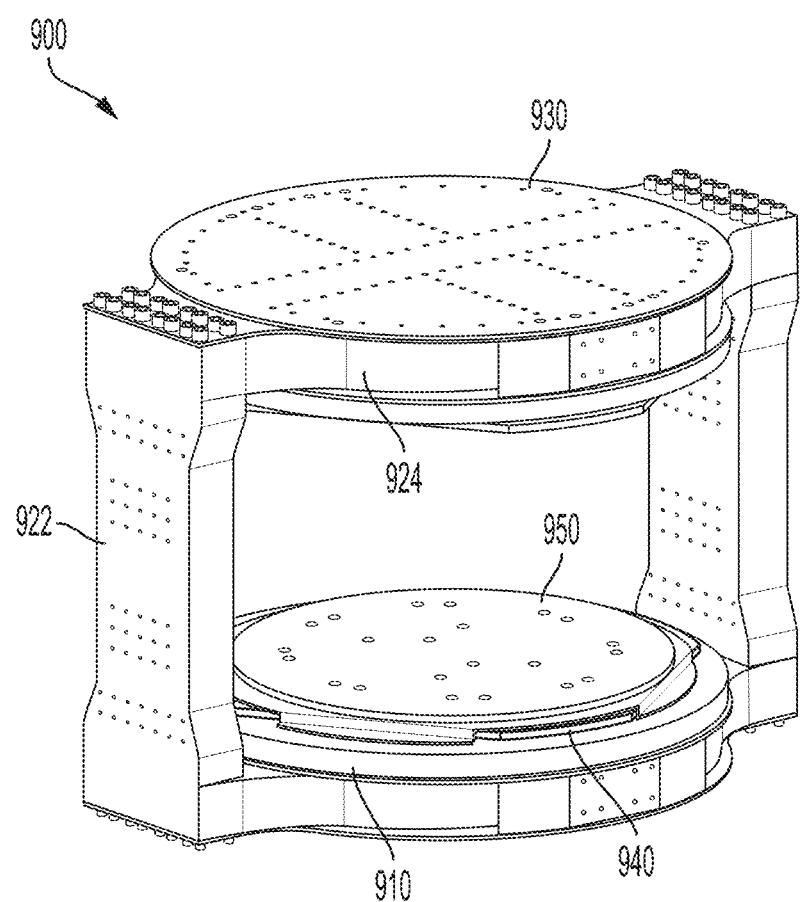
Figure 9D:
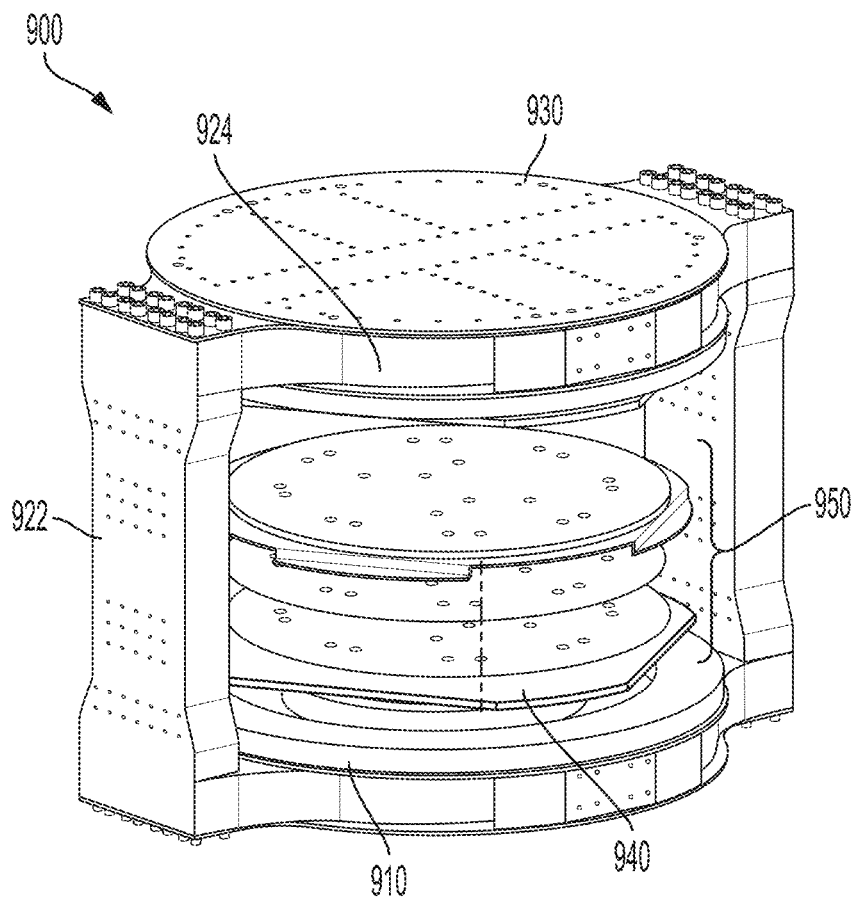

As described herein, in some embodiments, the blades may be arranged in a radial manner. However, in some embodiments, an alternative arrangement may be employed. One example of such alternative arrangement is shown in FIGS. 9A-9D, which depict different views of an apparatus 900 for providing a $B_0$ magnetic field for an MRI system, the assembly including ferromagnetic connectors and blades, in accordance with some embodiments of the technology described herein. FIG. 9A shows the apparatus 900 in a partially disassembled state, and FIG. 9B shows a top view of the apparatus 900 in a partially disassembled state. FIGS. 9C and 9D show the apparatus 900 assembled with laminate panels 940 and shims 950 and in an exploded view, respectively.

For example, in some embodiments and as shown in FIGS. 9A and 9B, apparatus 900 includes $B_0$ magnets 910 and a frame that captures electromagnetic flux produced by the $B_0$ magnet 910 and transfers the flux to the opposing permanent magnet to increase the flux density between $B_0$ magnets 910. The $B_0$ magnets 910 are arranged in a bi-planar geometry and may each include, for example, a plurality of concentric permanent magnet rings as described in connection with the embodiment of FIG. 2.

In some embodiments, the frame includes posts 922 coupled to multi-pronged members 924, as described in connection with the example of FIG. 2. The frame also includes one or more connectors 925 extending between opposite ends of posts 922. The connectors 925 may secure the posts 922 to one another. The connectors 925 may be positioned between the multi-pronged members 924, in some embodiments.

In some embodiments, the connectors 925 may be elongated bars extending between the posts 922. The bars may have intermediate portions with a reduced thickness relative to end portions of the bars, as shown in FIG. 9B. In some embodiments, the frame may include multiple connectors 925 (e.g., two, two or more, etc.), and the connectors 925 may be positioned substantially parallel one another. The connectors 925 may also be positioned substantially parallel to a direction of one of the gradient fields (e.g., one of the X- or Y-gradient fields) to enhance the generated gradient field strength during MR imaging.

In some embodiments, there may be a gap G1 between the intermediate portions of the connectors 925. The gap G1 may be approximately 80 mm in width or may be in a range from 75 mm to 100 mm in width. Alternatively, in some embodiments, the width of gap G1 may be determined relative to a length of the posts 922 (e.g., a distance between opposing multi-pronged members 924 of the frame). For example, the width of gap G1 may be less than a quarter of the length of the posts 922. Limiting the width of gap G1 and the thickness of connectors 925 may reduce the magnitude of eddy currents circulating through the frame during MR imaging.

In some embodiments, the frame, including posts 922, multi-pronged members 924, and connectors 925, may be constructed of any desired ferromagnetic material, for example, low carbon steel and/or CoFe, and/or silicon steel, etc. to provide the desired magnetic properties for the frame. In some embodiments, posts 922, multi-pronged members 924, and/or connectors 925 may be constructed of laminated ferromagnetic material (e.g., any of the aforementioned ferromagnetic materials) in order to reduce persistent circulation of eddy currents around the cross-section of the multi-pronged members 924 and/or connectors 925. In such embodiments, first and second posts 922, multi-pronged members 924, and/or connectors 925 may be formed of laminations disposed in planes substantially orthogonal to the planes in which the rings of $B_0$ magnets 910 are positioned.

In some embodiments, apparatus 900 may include blades 926. Blades 926 may be similar to blades 340 of apparatus 300, as described in connection with FIG. 3. Blades 926, however, may be arranged substantially parallel to a direction of one of the gradient fields (e.g., one of the X- or Y-gradient fields) rather than in a radial arrangement as in apparatus 300. Blades 926 may be arranged substantially parallel to a direction of one of the gradient fields to provide improved gradient field efficiency during operation of the MRI system. The apparatus 900 may include a number of blades 926, such as 4 or 6 blades, to provide the improved gradient field efficiency. Alternatively, the apparatus 900 may include a number of blades 926 in a range from 2 to 8 blades. In the examples of FIGS. 9A and 9B, four blades 926 are shown, positioned in pairs on either side of the connectors 925. The blades 926 of each pair may be separated by a gap G2 having a width of approximately 127.4 mm. In some embodiments, the gap G2 may have a width in a range from 110 mm to 140 mm.

In some embodiments, to provide improved gradient field efficiency, blades 926 may be formed of a ferromagnetic material. The blades may be formed of, for example, low carbon steel, CoFe, and/or silicon steel to provide the desired magnetic properties. The blades 926 may be formed of a same ferromagnetic material as the other components of the frame or may be formed of a different ferromagnetic material as the frame.

In some embodiments, blades 926 may be formed separately from the multi-pronged members 924 and/or connectors 925. In such embodiments, the blades 926 may be formed by, for example, stamping or laser cutting from sheet metal stock. Alternatively, blades 926, multi-pronged members 924, and connectors 925 may be cast together as a single piece to reduce the number of parts needed for assembly.

In some embodiments, blades 926 may have constant profiles along their lengths, similar to the example of blade 340 depicted in FIG. 4A. FIG. 4A shows an example of a blade having a constant height H and a constant width W along its length. In some embodiments, blades 926 may have a constant width of approximately 7.5 mm or a constant width in a range from 5 mm to 10 mm. In some embodiments, blades 926 may have a constant height of approximately 66 mm or a constant height in a range from 50 mm to 100 mm. In some embodiments, blades 926 may have a constant length of approximately 190 mm or in a range from 170 mm to 210 mm.

In some embodiments, blades 926, multi-pronged members 924, and/or connectors 925 may attach to non-conductive components configured to support the apparatus 900 and $B_0$ magnets 910. For example, each multi-pronged member 924 may be secured to and spaced apart from an opposing multi-pronged member 924 by spacers 928. In some embodiments, spacers 928 may be formed of plastic or any other suitable non-conductive material. Additionally, spacers 928 may be configured to provide rigidity non-conductive supports 930.

In some embodiments, the apparatus may include one or more non-conductive supports 930 configured to cover the components of the frame and provide support to $B_0$ magnets 910 and blades 926. In some embodiments, structural foam may be inserted into the spaces between the non-conductive supports 930, multi-pronged members 924, connectors 925, and/or blades 926. The non-conductive supports 930 may be formed of a non-conductive laminate material such as G-10. The non-conductive supports 930 may be positioned on an outward-facing surface of the multi-pronged members 924 and/or between an inward-facing surface of the multi-pronged members 924 and the $B_0$ magnets 910, where "inward-facing" indicates facing towards the region between the $B_0$ magnets 910. Because the blades 926 are secured to non-conductive supports 930 rather than multi-pronged members 924, no slots in multi-pronged members 924 may be machined, reducing manufacturing complexity of the apparatus 900 relative to the apparatus 300 and/or 600.

In some embodiments, the non-conductive supports 930 may be fastened to the multi-pronged members 924 and connectors 925 by fasteners 932, in some embodiments. The fasteners may extend through the multi-pronged members 924 and/or connectors 925 into posts 922. Additionally, in some embodiments, blades 926 may be fastened to non-conductive supports 930 by additional fasteners (not shown) extending through the non-conductive supports 930 into blades 926.

In some embodiments, apparatus 900 may include laminate panels 940 and/or shims 950, as shown in the examples of FIGS. 9C and 9D. Laminate panels 940 may be positioned on inward-facing surfaces of $B_0$ magnets 910, and shims 950 may be placed on laminate panels 940 thereafter. In some embodiments, laminate panels 940 may include at least one conductive layer patterned to form one or more gradient coils, or a portion of one or more gradient coils, capable of producing or contributing to magnetic fields suitable for providing spatial encoding of detected MR signals when operated in a low-field MRI apparatus. In some embodiments, the laminate panel may comprise one or more conductive layers patterned to form one or more X-gradient coils (or portions thereof), one or more Y-gradient coils (or portions thereof) and/or one or more Z-gradient coils (or portions thereof).

Alternatively or additionally, laminate panels 940 may include at least one conductive layer patterned to form one or more transmit and/or receive coils, or a portion of one or more transmit and/or receive coils, configured to stimulate an MR response by producing a $B_1$ excitation field (transmit) and/or receive an emitted MR signal (receive) when operated in conjunction with magnetic components configured to produce a $B_0$ field and/or corresponding gradient fields for spatially encoding received MR signals. Furthermore, in some embodiments, the laminate panels 940 may include additional magnetic components such as one or more shim coils arranged to generate magnetic fields in support of the system to, for example, increase the strength and/or homogeneity of the B0 field, counteract deleterious field effects such as those created by operation of the gradient coils, loading effects of the object being imaged, or to otherwise support the magnetics of the low field MRI system. Additional details regarding the fabrication and structure of such laminate panels is provided in U.S. Pat. No. 10,495,712 filed on Sep. 29, 2017 and titled "Low Field Magnetic Resonance Imaging Methods and Assembly," which is incorporated herein by reference in its entirety.

In some embodiments, shims 950 may be positioned adjacent laminate panels 940 and configured to improve homogeneity and provide correction to the field strength of the $B_0$ magnetic field within the imaging region of the MRI system. For example, passive pieces of ferromagnetic material (e.g., steel) may be positioned to adjust the $B_0$ magnetic field profile of the MRI system. Shims 950, for example, may be formed as sheets of magnetic material that have been magnetized in a desired pattern to produce a magnetic field to improve the profile of the B0 magnetic field. Shims 950 are shown in the example of FIG. 9B as including two sheets of magnetic material (lower sheets) and a plastic retainer (top) configured to locate the orientation of and secure the shims to the laminate panels 940. It should be appreciated that shims 950 may include fewer or more than two sheets of magnetic material in some embodiments. Additional details regarding the fabrication and structure of magnetic sheet shims is provided in U.S. Pat. No. 10,613,168 filed Mar. 22, 2017 and titled "Methods and Apparatus for Magnetic Field Shimming," which is incorporated by reference herein in its entirety.

Figure 10A:
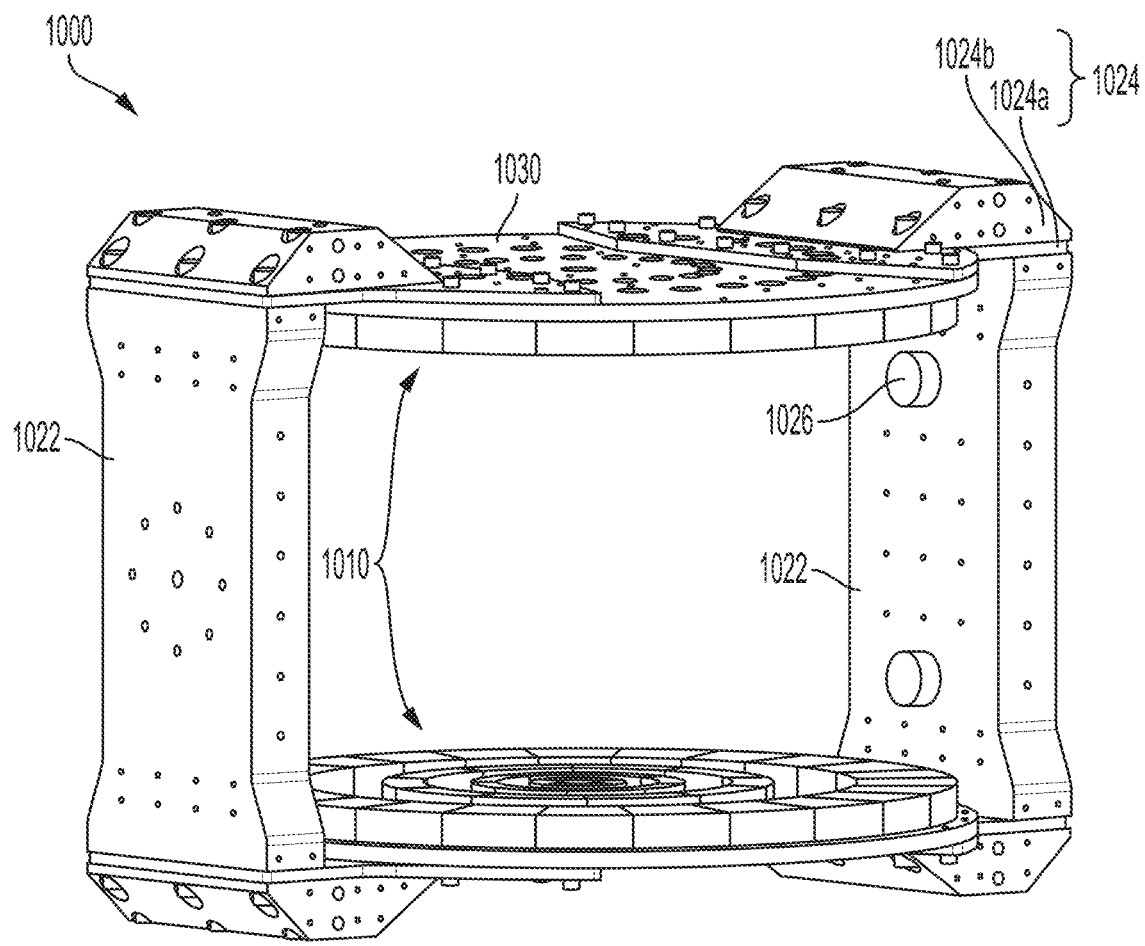
FIGS. 10A-10B illustrate views of an apparatus for providing a $B_0$ magnetic field for an MRI system, the assembly including ferromagnetic plates and connection assemblies, in accordance with some embodiments of the technology described herein.
Figure 10B:
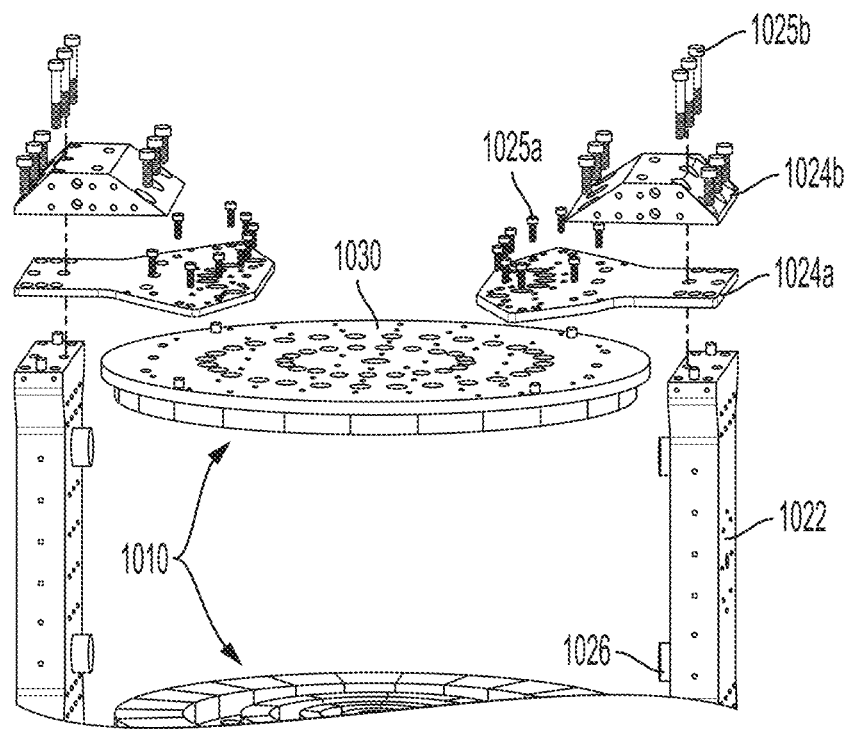

FIGS. 10A-10B illustrate views of an apparatus 1000 for providing a $B_0$ magnetic field for an MRI system, in accordance with some embodiments of the technology described herein. In some embodiments, the apparatus 1000 includes posts 1022 secured to plates 1030 by connection assemblies 1024. The plates 1030 may be configured to support the $B_0$ magnets 1010.

In some embodiments, the connection assemblies 1024 may include a first connector 1024a and a second connector 1024b. The first connector 1024a may connect one of the posts 1022 to one of the plates 1030. For example, and as shown in FIG. 10B, the first connector 1024a may be a substantially planar plate extending over the plate 1030 so that fasteners 1025a may extend through the first connector 1024a and secure the first connector 1024a to the plate 1030. First connector 1024a may be secured to the post 1022 by additional fasteners 1025b extending through the second connector 1024b, the first connector 1024a, and the post 1022. Forming the connection assembly 1024 out of multiple "layered" components may reduce manufacturing costs (e.g., by simplifying machining processes). In some embodiments, insulating components (not shown) may be inserted between components of the connection assembly 1024 and/or between the connection assembly 1024 and the post 1022 to reduce or mitigate eddy current circulation in the apparatus 1000.

In some embodiments, the second connector 1024b may be configured to increase the magnetic flux capacity of the apparatus 1000. For example, the second connector 1024b may have a wedge-like shape as shown in the examples of FIGS. 10A and 10B to direct and concentrate magnetic flux from the posts 1022 back into the imaging region between the $B_0$ magnets 1010.

In some embodiments, plates 1030 may be configured to support $B_0$ magnets 1010. Plates 1030 may be formed from solid ferromagnetic sheet material. In some embodiments, plates 1030 may include one or more holes to reduce the weight of the plates 1030 and/or to allow for cooling or venting of the apparatus 1000 during MR imaging.

In some embodiments, posts 1022, connection assemblies 1024, and plates 1030 may be constructed of any desired ferromagnetic material, for example, low carbon steel and/or CoFe, and/or silicon steel, etc. to provide the desired magnetic properties for the apparatus 1000. In some embodiments, posts 1022, connection assemblies 1024, and/or plates 1030 may be constructed of laminated ferromagnetic material (e.g., any of the aforementioned ferromagnetic materials) in order to reduce persistent circulation of eddy currents around the cross-section of the connection assemblies 1024 or plates 1030. In such embodiments, posts 1022, connection assemblies 1024, and/or plates 1030 may be formed of laminations disposed in planes substantially orthogonal to the planes of $B_0$ magnets 1010.

In some embodiments, apparatus 1000 may include additional permanent magnets 1026 positioned on inward-facing surfaces of posts 1022. The permanent magnets 1026 may be positioned and/or shaped to reduce inhomogeneity of the $B_0$ magnetic field and may be used in addition to or as a replacement for shim coils and/or passive shims positioned adjacent the $B_0$ magnets 1010. For example, the permanent magnets 1026 may be cylindrical or elliptical in cross-sectional shape. The permanent magnets 1026 may be disposed along the length of posts 1022.

In some embodiments, permanent magnets 1026 may be polarized along a direction perpendicular to a plane of the inward-facing surfaces of the posts 1022 (e.g., toward or away from a common center of the concentric $B_0$ permanent magnet rings 1010). In some embodiments having two permanent magnets 1026, each of the two permanent magnets 1026 may have opposing polarizations. For example, a first of the permanent magnets 1026 may have a polarization directed toward the inward-facing surfaces of the posts 1022 and a second of the permanent magnets 1026 may have a polarization direction away from the inward-facing surfaces of the posts 1022.

It should be appreciated that while the examples of FIGS. 10A and 10B show two permanent magnets 1026 attached to each post 1022, additional permanent magnets 1026 or fewer permanent magnets 1026 may be used in some embodiments. It should also be appreciated that permanent magnets 1026 may be included in any of the embodiments described herein, including apparatuses 200, 300, 600, 900, and/or 1000.

Having thus described several aspects of at least one embodiment of this technology, it is to be appreciated that various alterations, modifications, and improvements will readily occur to those skilled in the art.

Various aspects of the technology described herein may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The terms "approximately," "substantially," and "about" may be used to mean within ±20% of a target value in some embodiments, within ±10% of a target value in some embodiments, within ±5% of a target value in some embodiments, within ±2% of a target value in some embodiments. The terms "approximately," "substantially," and "about" may include the target value.

What is claimed is:

1. An apparatus for providing a $B_0$ magnetic field for a magnetic resonance imaging (MRI) system, the apparatus comprising:
   at least one permanent $B_0$ magnet to contribute a magnetic field to the $B_0$ magnetic field for the MRI system; and
   a ferromagnetic frame configured to capture and direct at least some of the magnetic field generated by the at least one permanent $B_0$ magnet, the frame comprising:
      a first post having a first end and a second end;
      a first multi-pronged member coupled to the first end and comprising a stem and two prongs coupled to the stem; and
      a second multi-pronged member coupled to the second end,
      wherein the first and second multi-pronged members support the at least one permanent $B_0$ magnet.

2. The apparatus of claim 1, wherein the ferromagnetic frame further comprises:
   a second post having a third end and a fourth end;
   a third multi-pronged member coupled to the third end; and
   a fourth multi-pronged member coupled to the fourth end.

3. The apparatus of claim 2, wherein the first post and the second post are secured to one another by at least one ferromagnetic connector.

4. The apparatus of claim 3, wherein the at least one ferromagnetic connector comprises a first bar and a second bar, wherein the first bar is positioned substantially parallel to the second bar and wherein a portion of the first bar is separated from a portion of the second bar by a gap.

5. The apparatus of claim 3, wherein the at least one ferromagnetic connector further comprises at least one blade having a length extending along a direction substantially perpendicular to a length of the at least one ferromagnetic connector.

6. The apparatus of claim 2, wherein each of the first post, first multi-pronged member, second multi-pronged member, second post, third multi-pronged member, and fourth multi-pronged member comprises ferromagnetic material.

7. The apparatus of claim 2, wherein the two prongs are spaced apart from one another by a gap and each of the two prongs is curved.

8. The apparatus of claim 2, wherein:
   the first multi-pronged member is disposed opposite the third multi-pronged member with a gap between the first and third multi-pronged member; and
   the second multi-pronged member is disposed opposite the fourth multi-pronged member with a gap between the second and the fourth multi-pronged member.

9. The apparatus of claim 2, wherein the at least one permanent $B_0$ magnet is a bi-planar magnet comprising first concentric permanent magnet rings and second concentric permanent magnet rings,
   the first and third multi-pronged members support the first concentric permanent magnet rings, and
   the second and fourth multi-pronged members support the second concentric permanent magnet rings.

10. The apparatus of claim 2, further comprising a first plurality of ferromagnetic blades and a second plurality of ferromagnetic blades, wherein:
    an end of each of the first plurality of ferromagnetic blades is coupled to the first multi-pronged member or the third multi-pronged member,
    an end of each of the second plurality of ferromagnetic blades is coupled to the second multi-pronged member or the fourth multi-pronged member, and
    ferromagnetic blades of the first and second pluralities of ferromagnetic blades are arranged to extend radially from a common center.

11. A magnetic resonance imaging system, comprising:
    the apparatus of claim 1;
    a plurality of gradient coils configured to, when operated, generate magnetic fields to provide spatial encoding of emitted magnetic resonance signals;
    at least one radio frequency transmit coil; and
    a power system configured to provide power to the plurality of gradient coils and the at least one radio frequency transmit coil.

12. A method, comprising:
    imaging a patient using a magnetic resonance imaging (MRI) system, the MRI system comprising:
       at least one permanent $B_0$ magnet to contribute a magnetic field to a $B_0$ magnetic field for the MM system; and
       a ferromagnetic frame configured to capture and direct at least some of the magnetic field generated by the at least one permanent $B_0$ magnet, the ferromagnetic frame comprising:
          a first post having a first end and a second end;
          a first multi-pronged member coupled to the first end and comprising a stem and two prongs coupled to the stem; and
          a second multi-pronged member coupled to the second end,
          wherein the first and second multi-pronged members support the at least one permanent $B_0$ magnet.

13. A frame for capturing and directing at least some of a $B_0$ magnetic field generated by a magnetic resonance imaging (MM) system, the frame comprising:
    a ferromagnetic frame configured to capture and direct at least some of the $B_0$ magnetic field generated by at least one permanent $B_0$ magnet, the ferromagnetic frame comprising:
       a first post having a first end and a second end;
       a first multi-pronged member coupled to the first end and comprising a stem and two prongs coupled to the stem; and
       a second multi-pronged member coupled to the second end,
       wherein the first and second multi-pronged members support the at least one permanent $B_0$ magnet.

14. The frame of claim 13, wherein the ferromagnetic frame further comprises:
    a second post having a third end and a fourth end;
    a third multi-pronged member coupled to the third end; and
    a fourth multi-pronged member coupled to the fourth end.

15. The frame of claim 14, further comprising at least one spacer securing the first multi-pronged member to the third multi-pronged member and securing the second multi-pronged member to the fourth multi-pronged member.

16. The frame of claim 14, further comprising a first plurality of ferromagnetic blades.

17. The frame of claim 16, wherein each of the first plurality of ferromagnetic blades is arranged to extend along a direction substantially parallel to one of an x- or y-gradient magnetic field.

18. The frame of claim 16, wherein the first post and the second post are secured to one another by at least one bar, and wherein each of the first plurality of ferromagnetic blades is arranged to extend along a direction substantially perpendicular to a length of the at least one bar.

19. The frame of claim 14, further comprising at least one first permanent magnet coupled to an interior face of the first post and at least one second permanent magnet coupled to an interior face of the second post.

20. The frame of claim 19, wherein:
the at least one first permanent magnet comprises a first permanent magnet having a first polarization directed toward the interior face of the first post and a second permanent magnet having a second polarization opposite the first polarization, and
the at least one second permanent magnet comprises a third permanent magnet having a third polarization directed toward the interior face of the second post and a fourth permanent magnet having a fourth polarization opposite the third polarization.

* * * * *

UNITED STATES PATENT AND TRADEMARK OFFICE
CERTIFICATE OF CORRECTION

| | | |
|---|---|---|
| PATENT NO. | : 11,971,465 B2 | Page 1 of 1 |
| APPLICATION NO. | : 17/884078 | |
| DATED | : April 30, 2024 | |
| INVENTOR(S) | : Cedric Hugon, Hadrien A. Dyvorne and Michael Stephen Poole | |

It is certified that error appears in the above-identified patent and that said Letters Patent is hereby corrected as shown below:

In the Claims

Column 20, Line 49: replace "(MM)" with --(MRI)--

Signed and Sealed this
Twenty-fourth Day of June, 2025

Coke Morgan Stewart
*Acting Director of the United States Patent and Trademark Office*